(12) United States Patent
Béliveau et al.

(10) Patent No.: US 9,221,867 B2
(45) Date of Patent: Dec. 29, 2015

(54) METHOD FOR TRANSPORTING A COMPOUND ACROSS THE BLOOD-BRAIN BARRIER

(75) Inventors: Richard Béliveau, Montréal (CA); Michel Demeule, Beaconsfield (CA)

(73) Assignee: Angiochem Inc., Montreal (CA)

( * ) Notice: Subject to any disclaimer, the term of this patent is extended or adjusted under 35 U.S.C. 154(b) by 1749 days.

(21) Appl. No.: 10/541,304

(22) PCT Filed: Jan. 5, 2004

(86) PCT No.: PCT/CA2004/000011
§ 371 (c)(1),
(2), (4) Date: Oct. 6, 2008

(87) PCT Pub. No.: WO2004/060403
PCT Pub. Date: Jul. 22, 2004

(65) Prior Publication Data
US 2006/0182684 A1    Aug. 17, 2006

Related U.S. Application Data

(60) Provisional application No. 60/437,986, filed on Jan. 6, 2003.

(51) Int. Cl.
C07K 14/47 (2006.01)
C07H 21/00 (2006.01)
A61K 38/00 (2006.01)

(52) U.S. Cl.
CPC .............. *C07H 21/00* (2013.01); *C07K 14/47* (2013.01); *A61K 38/00* (2013.01)

(58) Field of Classification Search
None
See application file for complete search history.

(56) References Cited

U.S. PATENT DOCUMENTS

| | | |
|---|---|---|
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,126,249 A | 6/1992 | Becker et al. |
| 5,169,933 A | 12/1992 | Anderson et al. |
| 5,204,354 A | 4/1993 | Chakravarty et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,442,043 A | 8/1995 | Fukuta et al. |
| 5,506,120 A * | 4/1996 | Yamamoto et al. ........... 435/69.7 |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,869,045 A | 2/1999 | Hellstrom et al. |
| 5,922,754 A | 7/1999 | Burchett et al. |
| 5,948,750 A | 9/1999 | Garsky et al. |
| 5,948,888 A | 9/1999 | de la Monte et al. |
| 5,955,444 A | 9/1999 | Ingram et al. |
| 5,962,266 A | 10/1999 | White et al. |
| 5,981,564 A | 11/1999 | Pagé et al. |
| 6,093,692 A | 7/2000 | Shen et al. |
| 6,126,965 A | 10/2000 | Kasid et al. |
| 6,191,290 B1 | 2/2001 | Safavy |
| 6,245,359 B1 | 6/2001 | Milstein et al. |
| 6,306,993 B1 | 10/2001 | Rothbard et al. |
| 6,310,039 B1 | 10/2001 | Kratz |
| 6,316,024 B1 | 11/2001 | Allen et al. |
| 6,348,207 B1 | 2/2002 | Milstein et al. |

(Continued)

FOREIGN PATENT DOCUMENTS

| | | |
|---|---|---|
| CA | 2283474 | 9/1998 |
| CA | 2421042 | 5/2002 |

(Continued)

OTHER PUBLICATIONS

Oldendorf WH 'Stereospecificity of blood-brain barrier permeability to amino acids' American Journal of Physiology v224(4) Apr. 1973 pp. 967-969.*
Henderson et al 'Terminal amino acid sequences and proteolytic cleavage sites of mouse mammary tumor virus any gene products' Journal of Virology Oct. 1983 pp. 314-319.*
Becker Y 'Putative antigenic domains in glycoprotein G of rabies virus: is the RGK sequence involved in virus adsorption to cellular receptors' Virus genes 3:3 1990 pp. 277-284.*
Chu et al ('1H NMR spectra of diasteromeric aromatic dipeptides (Phe-Phe) in aqueous solution' Magnetic Resonance in Chemistry v23(6) 1985 pp. 450-453.*

(Continued)

*Primary Examiner* — James H Alstrum Acevedo
*Assistant Examiner* — Ronald Niebauer
(74) *Attorney, Agent, or Firm* — Clark & Elbing LLP; Kristina Bieker-Brady

(57) ABSTRACT

The present invention relates to improvements in the field of drug delivery. More particularly, the invention relates to a non-invasive and flexible method and carrier for transporting a compound or drug across the blood-brain barrier of an individual. In particular the present invention relates to a carrier for transporting an agent attached thereto across a blood-brain barrier, wherein the carrier is able to cross the blood-brain barrier after attachment to the agent and thereby transport the agent across the blood-brain barrier. The present invention relates to improvements in the field of drug delivery. More particularly, the invention relates to a non-invasive and flexible method and carrier for transporting a compound or drug across the blood-brain barrier of an individual. In particular the present invention relates to a carrier for transporting an agent attached thereto across a blood-brain barrier, wherein the carrier is able to cross the blood-brain barrier after attachment to the agent and thereby transport the agent across the blood-brain barrier.

20 Claims, 20 Drawing Sheets

(56) References Cited

U.S. PATENT DOCUMENTS

| | | |
|---|---|---|
| 6,376,648 B2 | 4/2002 | White et al. |
| 6,391,305 B1 | 5/2002 | Feng et al. |
| 6,469,047 B1 | 10/2002 | Jackson et al. |
| 6,475,481 B2 | 11/2002 | Talmadge |
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |
| 6,713,454 B1 | 3/2004 | Ekwuribe et al. |
| 6,906,033 B2 | 6/2005 | White et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 * | 3/2011 | Beliveau et al. ............. 514/21.4 |
| 8,530,429 B2 | 9/2013 | Robbins et al. |
| 8,569,323 B2 | 10/2013 | Ren et al. |
| 2002/0086384 A1 | 7/2002 | Levine et al. |
| 2003/0129186 A1 | 7/2003 | Beliveau et al. |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2009/0246211 A1 | 10/2009 | Henri et al. |
| 2010/0209429 A1 * | 8/2010 | Erlich et al. ............. 424/139.1 |
| 2010/0256055 A1 | 10/2010 | Castaigne et al. |
| 2010/0284921 A1 | 11/2010 | Gordon et al. |
| 2010/0297120 A1 | 11/2010 | Beliveau et al. |
| 2011/0059187 A1 | 3/2011 | Basu et al. |
| 2011/0305750 A1 | 12/2011 | Beliveau et al. |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0035069 A1 | 2/2013 | Fisher |
| 2013/0045873 A1 | 2/2013 | Hood et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |

FOREIGN PATENT DOCUMENTS

| | | | |
|---|---|---|---|
| CA | 2525236 | 1/2005 | |
| CA | 2637893 | 7/2007 | |
| CA | 2638034 | 7/2007 | |
| CN | 101262890 A | 9/2008 | |
| CN | 102406949 A | 4/2012 | |
| CN | 102552928 A | 7/2012 | |
| CN | 102614105 A | 8/2012 | |
| DE | 199 53 696 | 5/2001 | |
| EP | 0393431 | 10/1990 | |
| EP | 0393431 A1 | 10/1990 | |
| EP | 0495049 B1 | 7/1992 | |
| EP | 1466924 | 10/2004 | |
| EP | 1982699 A1 | 10/2008 | |
| EP | 2333074 A1 | 6/2011 | |
| GB | 2360453 | 1/2000 | |
| JP | 2007-509977 A | 4/2007 | |
| RU | 2172323 C2 | 10/1999 | |
| WO | WO 87/05702 | 9/1987 | |
| WO | WO 96/31531 | 10/1996 | |
| WO | WO 96/35788 | 11/1996 | ............. C12N 15/15 |
| WO | WO-96/39160 A1 | 12/1996 | |
| WO | WO 96/39183 | 12/1996 | |
| WO | WO 96/40210 | 12/1996 | |
| WO | WO 97/33996 | 9/1997 | ............. C12N 15/15 |
| WO | WO 97/40160 | 10/1997 | |
| WO | WO 97/40854 | 11/1997 | |
| WO | WO 99/46575 | 9/1999 | |
| WO | WO 00/01417 | 1/2000 | |
| WO | WO 01/30319 | 5/2001 | |
| WO | WO 02/33090 | 4/2002 | |
| WO | WO-02/43765 A2 | 6/2002 | |
| WO | WO-02/085923 A2 | 10/2002 | |
| WO | WO 03/009815 | 2/2003 | |
| WO | WO-03/102583 A1 | 12/2003 | |
| WO | WO 2004/060403 | 7/2004 | ............. A61K 47/48 |
| WO | WO 2004/060403 A3 | 7/2004 | |
| WO | WO-2004/093897 A1 | 11/2004 | |
| WO | WO-2004/108071 A2 | 12/2004 | |
| WO | WO 2005/002515 | 1/2005 | |
| WO | WO-2005/014625 A1 | 2/2005 | |
| WO | WO-2005/021579 A2 | 3/2005 | |
| WO | WO-2005/042029 A2 | 5/2005 | |
| WO | WO 2006/086870 | 8/2006 | |
| WO | WO-2006/089290 A1 | 8/2006 | |
| WO | WO-2006/108052 A2 | 10/2006 | |
| WO | WO-2006/138343 A2 | 12/2006 | |
| WO | WO 2007/009229 | 1/2007 | |
| WO | WO 2007/020085 | 2/2007 | |
| WO | WO 2007/030619 | 3/2007 | |
| WO | WO-2007/035716 A2 | 3/2007 | |
| WO | WO-2007/044323 A2 | 4/2007 | |
| WO | WO-2007/082978 A1 | 7/2007 | |
| WO | WO-2007/082979 A1 | 7/2007 | |
| WO | WO 2007/103515 | 9/2007 | |
| WO | WO 2007/113172 | 10/2007 | |
| WO | WO 2008/012629 | 1/2008 | |
| WO | WO-2008/036682 A2 | 3/2008 | |
| WO | WO 2008/046228 | 4/2008 | |
| WO | WO-2008/116171 A1 | 9/2008 | |
| WO | WO 2008/144919 | 12/2008 | |
| WO | WO 2009/039188 | 3/2009 | |
| WO | WO 2009/046220 | 4/2009 | |
| WO | WO 2009/070597 | 6/2009 | |
| WO | WO 2009/079790 | 7/2009 | |
| WO | WO 2009/105671 | 8/2009 | |
| WO | WO 2009/127072 | 10/2009 | |
| WO | WO-2010/006239 A2 | 1/2010 | |
| WO | WO 2010/043047 | 4/2010 | |
| WO | WO 2010/043049 | 4/2010 | |
| WO | WO 2010/063122 | 6/2010 | |
| WO | WO 2010/063123 | 6/2010 | |
| WO | WO 2010/063124 | 6/2010 | |
| WO | WO 2010/069074 | 6/2010 | |

(56) References Cited

FOREIGN PATENT DOCUMENTS

| | | |
|---|---|---|
| WO | WO-2010/121379 A1 | 10/2010 |
| WO | WO-2010/142035 A1 | 12/2010 |
| WO | WO-2011/000095 A1 | 1/2011 |
| WO | WO-2011/008823 A2 | 1/2011 |
| WO | WO-2011/041897 A1 | 4/2011 |
| WO | WO-2011/063507 A1 | 6/2011 |
| WO | WO-2011/112635 A1 | 9/2011 |
| WO | WO-2011/153642 A1 | 12/2011 |
| WO | WO-2012/000118 A1 | 1/2012 |
| WO | WO-2012/006239 A1 | 1/2012 |
| WO | WO-2012/037687 A1 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/153286 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/023184 A1 | 2/2013 |
| WO | WO-2013/032591 A1 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078562 A2 | 6/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |
| WO | WO-2013/185235 A1 | 12/2013 |

OTHER PUBLICATIONS

Waterbeemd et al ('Lipophilicity of amino acids' Amino Acids v7 1994 pp. 129-145).*
Patel et al ('Getting drugs into the brain:approaches to enhance brain drug delivery' CNS Drugs v23(1) 2009 pp. 35-58).*
Ziske et al (abstract retrieved from http://www.ncbi.nlm.nih.gov/pubmed/12056715 on Mar. 19, 2014, 1 page).*
Akhtar et al., "Nonviral Delivery of Synthetic siRNAs in Vivo," *J. Clin. Invest.* 117:3623-3632 (2007).
Anonymous, "Blood-Brain Barrier Tackled," <http:www.ecancermedicalscience.com/news-insider-news.asp?itemmId=326> Oct. 22, 2008.
Arpicco et al., "New Coupling Reagents for the Preparation of Disulfide Cross-Linked Conjugates with Increased Stability," *Bioconj. Chem.* 8:327-337 (1997).
Banks, "Leptin Transport Across the Blood-Brain Barrier: Implications for the Cause and Treatment of Obesity," *Curr. Pharm. Des.* 7:125-133 (2001).
Banks, "The Blood-Brain Barrier as a Cause of Obesity," *Curr. Pharm. Des.* 14:1606-1614 (2008).
Barakat et al., "Modulation of P-Glycoprotein Function by Caveolin-1 Phosphorylation," *J. Neurochem.* 101: 1-8 (2007).
Bertrand et al., "Transport Characteristics of a Novel Peptide Platform for CNS Therapeutics," *J. Cell Mol. Med.* published online Oct. 10, 2009. (available at http://dx.doi.org/10.1111/j.1582-4934.2009.00930.x).
Bicamumpaka et al., "In Vitro Cytotoxicity of Paclitaxel-Transferrin Conjugate on H69 Cells," *Oncol. Rep.* 5:1381-1383 (1998).
Boado, "Blood-brain Barrier Transport of Non-viral Gene and RNAi Therapeutics," *Pharm. Res.* 24:1772-1787 (2007).
Boules et al., "Bioactive Analogs of Neurotensin: Focus on CNS Effects," *Peptides.* 27:2523-2533 (2006).
Castex et al., "2-Pyrrolinodoxorubicin and Its Peptide-vectorized Form Bypass Multidrug Resistance," *Anticancer Drugs.* 15:609-617 (2004).
Chari et al., "Targeted Cancer Therapy: Conferring Specificity to Cytotoxic Drugs," *Acc. Chem. Res.* 41:98-107 (2008).
Che et al., "New Angiopep-Modified Doxorubicin (ANG1007) and Etoposide (ANG1009) Chemotherapeutics with Increased Brain Penetration," *J. Med. Chem.* 53:2814-2824 (2010).
Coon et al., "Solutol HS 15, Nontoxic Polyoxyethylene Esters of 12-hydroxystearic Acid, Reverses Multidrug Resistance," *Cancer Res.* 51:897-902 (1991).
D'Onofrio et al., "Glycomimetics as Decorating Motifs for Oligonucleotides: Solid-phase Synthesis, Stability, and Hybridization Properties of Carbopeptoid-oligonucleotide Conjugates," *Bioconjug. Chem.* 16:1299-1309 (2005).
Demeule et al., "Drug Transport to the Brain: Key Roles for the Efflux Pump P-Glycoprotein in the Blood-Brain Barrier," *Vascul. Pharmacol.* 38:339-348 (2002).
Demeule et al., "Identification and Design of Peptides as a New Drug Delivery System for the Brain," *J. Pharmacol. Exp. Ther.* 324:1064-1072 (2008).
Demeule et al., "Involvement of the Low-Density Lipoprotein Receptor-Related Protein in the Transcytosis of the Brain Delivery Vector Angiopep-2," *J. Neurochem.* 106:1534-1544 (2008).
Dooley et al., "An All D-amino Acid Opioid Peptide with Central Analgesic Activity from a Combinatorial Library," *Science.* 266: 2019-2022 (1994).
Eigenbrot et al., "X-Ray Structure of Glial Cell-Derived Neurotrophic Factor at 1.9 Å Resolution and Implications for Receptor Binding," *Nat. Struct. Biol.* 4:435-438 (1997).
Gabius et al., "Targeting of Neoglycoprotein-Drug Conjugates to Cultured Human Embryonal Carcinoma Cells,"*J. Cancer Res. Clin. Oncol.* 113:126-130 (1987).
Garsky et al., "The Synthesis of a Prodrug of Doxorubicin Designed to Provide Reduced Systemic Toxicity and Greater Target Efficacy," *J. Med. Chem.* 44: 4216-4224 (2001).
Gelmon, "The Taxoids: Paclitaxel and Docetaxel," *Lancet.* 344:1267-1272 (1994).
Gewirtz, "A Critical Evaluation of the Mechanisms of Action Proposed for the Antitumor Effects of the Anthracycline Antibiotics Adriamycin and Daunorubicin," *Biochem. Pharmacol.* 57:727-741 (1999).
Gottschalk et al., "Protein Self-Association in Solution: The Bovine Pancreatic Trypsin Inhibitor Decamer," *Biophys. J.* 84: 3941-3958 (2003).
Harkavyi et al., "Glucagon-Like Peptide 1 Receptor Stimulation Reverses Key Deficits in Distinct Rodent Models of Parkinson's Disease," *J. Neuroinflammation.* 5:19 (2008) (pp. 1-9).
Huang et al., "Targeting Delivery of Paclitaxel into Tumor Cells via Somatostatin Receptor Endocytosis," *Chem. Biol.* 7:453-461 (2000).
Jodoin et al., "P-Glycoprotein in Blood-Brain Barrier Endothelial Cells: Interaction and Oligomerization With Caveolins," *J. Neurochem.* 87:1010-1023 (2003).
Kalra, "Central Leptin Insufficiency Syndrome: An Interactive Etiology for Obesity, Metabolic and Neural Diseases and for Designing New Therapeutic Interventions," *Peptides.* 29:127-138 (2008).
Karyekar et al., "Zonula Occludens Toxin Increases the Permeability of Molecular Weight Markers and Chemotherapeutic Agents Across the Bovine Brain Microvessel Endothelial Cells," *J. Pharm. Sci.* 92:414-423 (2003).
Ke et al., "Gene Delivery Targeted to the Brain Using an Angiopep-Conjugated Polyethyleneglycol-Modified Polyamidoamine Dendrimer," *Biomaterials*.30:6976-6985 (2009) (pp. 1-10).
Kilic et al., "Intravenous TAT-GDNF is Protective after Focal Cerebral Ischemia in Mice," *Stroke.* 34: 304-1310 (2003).
Kirsch et al., "Anti-Angiogenic Treatment Strategies for Malignant Brain Tumors," *J. Neurooncol.* 50:149-163 (2000).
Kounnas et al., "LDL Receptor-Related Protein, a Multifunctional ApoE Receptor, Binds Secreted Beta-Amyloid Precursor Protein and Mediates Its Degradation," *Cell.* 82:331-340 (1995).
Koziara et al., "In Situ Blood-Brain Barrier Transport of Nanoparticles," *Pharma. Res.* 20:1772-1778 (2003).
Kreuter, "Nanoparticulate Carries for Drug Delivery to the Brain," in *Nanoparticles as Drug Carriers*, Chapter 24, pp. 527-547, Torchilin VP, Imperial College Press, London (2006).

(56) References Cited

OTHER PUBLICATIONS

Kreuter et al., "Direct Evidence That Polysorbate-80-Coated Poly (Butylcyanoacrylate) Nanoparticles Deliver Drugs to the CNS Via Specific Mechanisms Requiring Prior Binding of Drug to the Nanoparticles," *Pharm. Res.* 20:409-416 (2003).
Kumar et al., "Transvascular Delivery of Small Interfering RNA to the Central Nervous System," *Nature.* 448:39-43 (2007).
Lewis et al., "Maleimidocysteineamido-DOTA Derivatives: New Reagents for Radiometal Chelate Conjugation to Antibody Sulfhydryl Groups Undergo pH-Dependent Cleavage Reactions," *Bioconj. Chem.* 9:72-86 (1998).
Mathupala, "Delivery of Small Interfering RNA (siRNA) to the Brain," *Exp. Opin. Ther. Pat.* 19:137-140 (2009).
Mazel et al., "Doxorubicin-Peptide Conjugates Overcome Multidrug Resistance," *Anticancer Drugs.* 12:107-116 (2001).
Moestrup et al., "Evidence That Epithelial Glycoprotein 330/Megalin Mediates Uptake of Polybasic Drugs," *J. Clin. Invest.* 96:1404-1413 (1995).
Moore et al., "The Role of Flexible Tethers in Multiple Ligand-Receptor Bond Formation Between Curved Surfaces," *Biophys. J.* 91:1675-1687 (2006).
Muratovska et al., "Conjugate for Efficient Delivery of Short Interfering RNA (siRNA) Into Mammalian Cells," *FEBS Lett.* 558:63-68 (2004).
Niola et al., "A Plasmid-Enclosed VEGF siRNA Reduces Glioblastoma Angiogenesis and Its Combination With Interleukin-4 Blocks Tumor Growth in a Xenograft Mouse Model," *Canc. Biol. Ther.* 5:2:174-179 (2006).
Pardridge "Drug Targeting to the Brain," *Pharm. Res.* 24:1733-1744 (2007).
Peri et al., "D-Glucose as a Regioselectively Addressable Scaffold for Combinatorial Chemistry on Solid Phase," *J. Carbohydr. Chem.* 22:57-71 (2003).
Qu et al., "Carbohydrate-Based Micelle Clusters Which Enhance Hydrophobic Drug Bioavailability by Up to 1 Order of Magnitude," *Biomacromolecules.* 7:3452-3459 (2006).
Rawat et al., "Lipid Carriers: A Versatile Delivery Vehicle for Proteins and Peptides," *Yakugaku Zasshi.* 128:269-280 (2008).
Régina et al., "Antitumor Activity of ANG 1005, A Conjugate Between Paclitaxel and the New Brain Delivery Vector Angiopep-2," *Br. J. Pharmacol.* 155:185-197 (2008).
Rouselle et al., "New Advances in the Transport of Doxorubicin Through the Blood-Brain Barrier by a Peptide Vector-Mediated Strategy," *Mol. Pharmacol.* 57:679-686 (2000).
Saito et al., "Drug Delivery Strategy Utilizing Conjugation Via Reversible Disulfide Linkages: Role and Site of Cellular Reducing Activities," *Adv. Drug Deliv. Rev.* 55:199-215 (2003).
Samson et al., "Gene Therapy for Diabetes: Metabolic Effects of Helper-Dependent Adenoviral Exendin 4 Expression in a Diet-Induced Obesity Mouse Model," *Mol. Ther.* 16:1805-1812 (2008) (pp. 1-18).
Steiniger et al., "Chemotherapy of Glioblastoma in Rats Using Doxorubicin-Loaded Nanoparticles," *Int. J. Cancer.* 109: 759-767 (2004).
Takei et al., "A Small Interfering RNA Targeting Vascular Endothelial Growth Factor as Cancer Therapeutics," *Cancer. Res.* 64:3365-3370 (2004).
Trail et al., "Cure of Xenografted Human Carcinomas by BR96-Doxorubicin Immunoconjugates," *Science.* 261:212-215 (1993).
Turner et al., "RNA Targeting With Peptide Conjugates of Oligonucleotides, siRNA and PNA," *Blood Cells Mol. Dis.* 38:1-7 (2007).
Uekita et al., "Membrane-Type 1 Matric Metalloproteinase Cytoplasmic Tail-Binding Protein-1 Is a New Member of the Cupin Superfamily. A Possible Multifunctional Protein Acting as an Invasion Suppressor Down-Regulated in Tumors," *J. Biol. Chem.* 279:12734-12743 (2004).
Uekita et al., "Cytoplasmic Tail-Dependent Internalization of Membrand-Type 1 Matrix Metalloproteinase is Important for Its Invasion-Promoting Activity," *J Cell Biol.* 155:1345-1356 (2001).

Veronese et al., "PEGylation, Successful Approach to Drug Delivery," *Drug Discov. Today.* 10:1451-1458 (2005).
Wang et al., "DNA/Dendrimer Complexes Mediate Gene Transfer Into Murine Cardiac Transplants ex Vivo," *Mol. Ther.* 2: 602-608 (2000).
Xu et al., "In Vitro and In Vivo Evaluation of Actively Targetable Nanoparticles for Paclitaxel Delivery," *Int. J. Pharm.* 288:361-368 (2005).
Zhang et al., "siRNA-Containing Liposomes Modified With Polyarginine Effectively Silence the Targeted Gene," *J. Control Release.* 112:229-239 (2006).
Zhang et al., "Silencing The Epidermal Growth Factor Receptor Gene With RNAi May Be Developed as a Potential Therapy for Non Small Cell Lung Cancer," *Genet. Vaccines Ther.* 3:1-12 (2005).
Zhang et al., "Intravenous RNA Interference Gene Therapy Targeting the Human Epidermal Growth Factor Receptor Prolongs Survival in Intracranial Brain Cancer," *Clin, Cancer Res.* 10:3667-3677 (2004).
European Patent Office Communication Containing Extended Search Report of Application No. 10009847.4-1216, Dated Nov. 15, 2010 (8 pages).
Reply to Office Action pertaining to U.S. Appl. No. 11/185,947, Mailed Jun. 6, 2008 (14 pages).
Reply to Office Action pertaining to U.S. Appl. No. 11/185,947, filed Feb. 6, 2009 (11 pages).
European Patent Office Communication pertaining to European Patent Application No. 05 770 546.9, Dated Jan. 11, 2010 (5 pages).
Response to European Patent Office Communication pertaining to European Patent Application No. 05 770 546.9, filed Jul. 21, 2010 (16 pages).
European Patent Office Communication pertaining to European Patent Application No. 05 770 546.9, Dated Jan. 18, 2011 (4 pages).
Ballabh et al., "The Blood-Brain Barrier: An Overview Structure, Regulation, and Clinical Implications" *Neurobiology of Disease* 16:1-13 (2004).
Bickel et al., "Delivery of Peptides and Proteins Through the Blood-Brain Barrier" *Advanced Drug Delivery Reviews* 46:247-279 (2001).
Bork et al., "Go Hunting in Sequence Databases But Watch Out for the Traps" *Trends in Genetics* 12:425-427 (1996).
Bork, "Powers and Pitfalls in Sequence Analysis: The 70% Hurdle" *Genome Research* 10:398-400 (2000).
Brenner, "Errors in Genome Annotation" *Trends in Genetics* 15:132-133 (1999).
Deane et al., "LRP/Amyloid β-Peptide Interaction Mediates Differential Brain Efflux of Aβ Isoforms" *Neuron* 43:333-344 (2004).
Dehouck et al., "A New Function for the LDL Receptor: Transcytosis of LDL Across the Blood-Brain Barrier" *The Journal of Cell Biology* 138:877-889 (1997).
Dehouck et al., "Drug Transfer Across the Blood-Brain Barrier: Correlation Between In Vitro and In Vivo Models" *Journal of Neurochemistry* 58:1790-1797 (1992).
Demeule et al., "High Transcytosis of Melanotransferrin (P97) Across the Blood-Brain Barrier" *Journal of Neurochemistry* 83:924-933 (2002).
Demeule et al., "Isolation of Endothelial Cells from Brain, Lung, and Kidney: Expression of the Multidrug Resistance P-Glycoprotein Isoforms" *Biochemical and Biophysical Research Communications* 281:827-834 (2001).
Doerks et al., "Protein Annotation: Detective Work for Function Prediction" *Trends in Genetics* 14:248-250 (1998).
Fillebeen et al., "Receptor-Mediated Transcytosis of Lactoferrin Through the Blood-Brain Barrier" *The Journal of Biological Chemistry* 274:7011-7017 (1999).
Fromm, "P-Glycoprotein: A Defense Mechanism Limiting Oral Bioavailability and CNS Accumulation of Drugs" *International Journal of Clinical Pharmacology and Therapeutics* 38:69-74 (2000).
Grabb et al., "Neoplastic and Pharmacological Influence on the Permeability of an in vitro Blood-Brain Barrier" *Journal of Neurosurgery* 82:1053-1058 (1995).
Guillot et al., "Angiotensin Peptide Regulation of Bovine Brain Microvessel Endothelial Cell Monolayer Permeability" *Journal of Cardiovascular Pharmacology* 18:212-218 (1991).

(56) References Cited

OTHER PUBLICATIONS

Gumbleton et al., "Progress and Limitations in the Use of In Vitro Cell Cultures to Serve as a Permeability Screen for the Blood-Brain Barrier" *Journal of Pharmaceutical Sciences* 90:1681-1698 (2001).
Hawkins et al., "The Blood-Brain Barrier/Neurovascular Unit in Health and Disease" *Pharmacological Reviews* 57:173-185 (2005).
Hussain et al., "The Mammalian Low-Density Lipoprotein Receptor Family" *Annual Review of Nutrition* 19:141-172 (1999).
Ito et al., "Functional Characterization of the Brain-to-Blood Efflux Clearance of Human Amyloid-β Peptide (1-40) Across the Rat Blood-Brain Barrier" *Neuroscience Research* 56:246-252 (2006).
Kiernan et al., "Fluorescent-Labelled Aprotinin: A New Reagent for the Histochemical Detection of Acid Mucosubstances" *Histochemie* 34:77-84 (1973).
Kobayashi et al., "The Protease Inhibitor Bikunin, a Novel Anti-Metastatic Agent" *Biol. Chem.* 384:749-754 (2003).
Koo et al., "Differential Expression of Amyloid Precursor Protein mRNAs in Cases of Alzheimer's Disease and in Aged Nonhuman Primates" *Neuron* 2:97-104 (1990).
Kreuter et al., "Apolipoprotein-Mediated Transport of Nanoparticle-Bound Drugs Across the Blood-Brain Barrier" *Journal of Drug Targeting* 10:317-325 (2002).
Lai et al., "The Critical Component to Establish in vitro BBB Model: Pericyte" *Brain Research Reviews* 50:258-265 (2005).
Larionova et al., "Carbohydrate-Containing Derivatives of the Trypsin-Kallikrein Inhibitor Aprotinin from Bovine Organs" *Biol. Chem. Hoppe-Seyler* 366:743-748 (1985).
Larsson, "Megalin, an Endocytotic Receptor With Signalling Potential" *Acta Universitatis Upsaliensis Uppsala* 1-60 (2006).
Ma et al., "Cationic Charge-Dependent Hepatic Delivery of Amidated Serum Albumin" *Journal of Controlled Release* 102:583-594 (2005).
Marinò et al., "Megalin-Mediated Transcytosis of Thyroglobulin by Thyroid Cells is a Calmodulin-Dependent Process" *Thyroid* 10:461-469 (2000).
Marinò et al., "Transcytosis of Retinol-Binding Protein Across Renal Proximal Tubule Cells After Megalin (gp 330)-Mediated Endocytosis" *The Journal of the American Society of Nephrology* 12:637-648 (2001).
Martel et al., "Transport of Apolipoproteins E and J at the Blood-Brain Barrier Relevance to Alzheimer's Disease" *S.T.P. Pharma Sciences* 7:28-36 (1997).
McCarty, "Cell Biology of the Neurovascular Unit: Implications for Drug Delivery Across the Blood-Brain Barrier" *ASSAY and Drug Development Technologies* 3:89-95 (2005).
Ngo et al., "Computational Complexity: Protein Structure Prediction, and the Levinthal Paradox" *The Protein Folding Problem and Tertiary Structure Prediction* 491-495 (1994).
Orlando et al., "Identification of the Second Cluster of Ligand-Binding Repeats in Megalin as a Site for Receptor-Ligand Interactions" *Proceedings of the National Academy of Sciences* 94:2368-2373 (1997).
Pan et al., "Efficient Transfer of Receptor-Associated Protein (RAP) Across the Blood-Brain Barrier" *Journal of Cell Science* 117:5071-5078 (2004).
Pardridge "Blood-Brain Barrier Biology and Methodology" *Journal of NeuroVirology* 5:556-569 (1999).
Pardridge "CNS Drug Design Based on Principles of Blood-Brain Barrier Transport" *Journal of Neurochemistry* 70:1781-1792 (1998).
Prince et al., "Lipoprotein Receptor Binding, Cellular Uptake, and Lysosomal Delivery of Fusions Between the Receptor-Associated protein (RAP) and α-L-Iduronidase or Acid α-Glucosidase" *The Journal of Biological Chemistry* 279:35037-35046 (2004).
Ramakrishnan, "The Role of P-Glycoprotein in the Blood-Brain Barrier" *The Einstein Quarterly Journal of Biology and Medicine* 19:160-165 (2003).
Régina et al., "Differences in Multidrug Resistance Phenotype and Matrix Metalloproteinases Activity Between Endothelial Cells from Normal Brain and Glioma" *Journal of Neurochemistry* 84:316-324 (2003).

Scherrmann, "Drug Delivery to Brain Via the Blood-Brain Barrier" *Vascular Pharmacology* 38:349-354 (2002).
Schinkel, "P-Glycoprotein, a Gatekeeper in the Blood-Brain Barrier" *Advanced Drug Delivery Reviews* 36:179-194 (1999).
Seidel et al., "Effects of Trasylol on the Blood-Brain Barrier in Rats" *Naunyn-Schmiedeberg's Archives of Pharmacology* Springer. Berlin, DE 284: p. R73 (1974).
Shibata et al., "Clearance of Alzheimer's Amyloid-$\beta_{1-40}$ Peptide From Brain LDL Receptor-Related Protein-1 at the Blood-Brain Barrier" *The Journal of Clinical Investigation* 106:1489-1499 (2000).
Shiiki et al., "Brain Insulin Impairs Amyloid-β(1-40) Clearance From the Brain" *The Journal of Neuroscience* 24:9632-9637 (2004).
Shimura et al., "Transport Mechanism of a New Behaviorally Highly Potent Adrenocorticotropic Hormone (ACTH) Analog, Ebiratide, Through the Blood-Brain Barrier" *The Journal of Pharmacology and Experimental Therapeutics* 258:459-465 (1991).
Skolnick et al., "From Genes to Protein Structure and Function: Novel Applications of Computational Approaches in the Genomic Era" *Trends in Biotech* 18:34-39 (2000).
Smith, "Brain Perfusion Systems for Studies of Drug Uptake and Metabolism in the Central Nervous System" *Models for Assessing Drug Absorption and Metabolism* 285-307 (1996).
Smith et al., "The Challenges of Genome Sequence Annotation or 'The Devil is in the Details'" *Nature Biotechnology* 15:1222-1223 (1997).
Tamai et al., "Structure-Internalization Relationship for Absorptive-Mediated Endocytosis of Basic Peptides at the Blood-Bain Barrier" *The Journal of Pharmacology and Experimental Therapeutics* 280:410-415 (1997).
Temsamani et al., "Vector-Mediated Drug Delivery to the Brain" *Expert Opinion on Biological Therapy* 1:773-782 (2001).
Terasaki et al., "New Approaches to in vitro Models of Blood-Brain Barrier Drug Transport" *Drug Discovery Today* 8:944-954 (2003).
Triguero et al., "Capillary Depletion Method for Quantification of Blood-Brain Barrier Transport of Circulating Peptides and Plasma Proteins" *Journal of Neurochemistry* 54:1882-1888 (1990).
Wells, "Additivity of Mutational Effects in Proteins" *Biochemistry* 29:8509-8517 (1990).
Witt et al., "Peptide Drug Modifications to Enhance Bioavailability and Blood-Brain Barrier Permeability" *Peptides* 22:2329-2343 (2001).
Yepes et al., "Tissue-Type Plasminogen Activator Induces Opening of the Blood-Brain Barrier Via the LDL Receptor-Related Protein" *The Journal of Clinical Investigation* 112:1533-1540 (2003).
Zlokovic et al., "Glycoprotein 330/Megalin: Probable Role in Receptor-mediated Transport of Apolipoprotein J Alone and in a Complex With Alzheimer Disease Amyloid β at the Blood-Brain and Blood Cerebrospinal Fluid Barriers" *Proceedings of the National Academy of Sciences USA* 93:4229-4234 (1996).
European Patent Office Communication Containing Extended Search Report of Application No. 05770546.9-1212 / 1859041, Dated Sep. 8, 2008.
European Patent Office Communication Containing European Search Report of Application No. 04700102.9 Dated Jan. 26, 2007.
International Preliminary Report on Patentability of International Patent Application No. PCT/CA2004/000011 dated Jun. 1, 2005.
International Search Report of International Application No. PCT/CA2006/001165 dated Nov. 9, 2006.
Office Action pertaining to U.S. Appl. No. 11/185,947 mailed Mar. 27, 2007.
Office Action pertaining to U.S. Appl. No. 11/185,947 mailed Mar. 7, 2008.
Written Opinion of the International Searching Authority of International Application No. PCT/CA2004/000011 mailed on Jun. 1, 2005.
Dagenais st el., "Development of an In Situ Mouse Brain Perfusion Model and Its Application to *mdr 1 a* P-Glycoprotein-Deficient Mice", *Journal of Cerebral Blood Flow & Metabolism*, vol. 20(2):381-386, Feb. 2000.
Dehouck et al., "An Easier, Reproducible, and Mass-Production Method to Study the Blood-Brain Barrier In Vitro", *Journal of Neurochemistry*, 54:1798-1801, (1990).

(56) References Cited

OTHER PUBLICATIONS

Laccabue et al., "A Novel Taxane Active against an Orthotopically Growing Human Clioma Xenograft", *Cancer*, 92(12):3085-3092, (2001).
Reply to Office action in U.S. Appl. No. 11/185,947, filed Jun. 9, 2008.
Official Communication issued by the European Patent Office for European Patent Application No. 04700102.9, dated Jul. 19, 2007.
Response to Official Communication for European Patent Application No. 04700102.9, filed Mar. 31, 2008.
Official Communication issued by the European Patent Office for European Patent Application No. 04700102.9, dated Jun. 16, 2009.
Response to Official Communication for European Patent Application No. 04700102.9, filed Jul. 31, 2009.
Official Communication issued by the European Patent Office for European Patent Application No. 04700102.9, dated Sep. 2, 2009.
Response to Official Communication for European Patent Application No. 04700102.9, filed Jan. 22, 2010.
Summons from the European Patent Office to attend oral proceedings for European Application No. 04700102.9, dated Feb. 23, 2010.
Response to Summons to attend oral proceedings for European Application No. 04700102.9, filed Jul. 27, 2010.
Official Communication issued by the European Patent Office for European Patent Application No. 05770546.9, dated Jan. 11, 2010.
Response to Official Communication for European Patent Application No. 05770546.9, filed Jul. 21, 2010.
Official Communication issued by the European Patent Office for European Patent Application No. 05770546.9, dated Jan. 18, 2011.
Author manuscript of Howes et al., "Rapid induction of therapeutic hypothermia using convective-immersion surface cooling: Safety, efficacy and outcomes," published in final edited form as: Resuscitation. 81(4):388-392 (2010); (13 pages).
Belkin et al., "Matrix-dependent proteolysis of surface transglutaminase by membrane-type metalloproteinase regulates cancer cell adhesion and locomotion," J Biol Chem. 276(21):18415-18422 (2001).
Boado et al., "GDNF fusion protein for targeted-drug delivery across the human blood-brain barrier," Biotechnol Bioeng. 100(2):387-96 (2008).
Brady et al., "Drug design. Refelections on a peptide." Nature. 368(6473):692-693 (1994).
Buvanendran et al., "Recent advances in nonopioid analgesics for acute pain management," Tech Reg Anesth Pain Man. 11(1):19-26 (2007).
Carell et al., "A novel procedure for the synthesis of libraries containing small organic molecules," Angew Chem Int Ed Engl. 33(20):2059-2061 (1994).
Carell et al., "A solution-phase screening procedure for the isolation of active compounds from a library of molecules," Angew Chem Int Ed Engl. 33(20):2061-2064 (1994).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261:1303-1305 (1993).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmacol. 3(5):227-233 (2009).
Cull et al., "Screening for receptor ligands using large libraries of peptides linked to the C terminus of the lac repressor," Proc Natl Acad Sci U S A. 89(5): 1865-1869 (1992).
D'Ortho et al., "Membrane-type matrix metalloproteinases 1 and 2 exhibit broad-spectrum proteolytic capacities comparable to many matrix metalloproteinases," Eur J Biochem. 250(3): 751-757 (1997).
Declaration of Michel Demeule in European Patent Application No. 11010125 dated Sep. 24, 2012 (4 pages).

Demule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
DeWitt et al., "'Diversomers': an approach to nonpeptide, nonoligomeric chemical diversity," Proc Natl Acad Sci U S A. 90(15):6909-6913 (1993).
Erb et al., "Recursive deconvolution of combinatorial chemical libraries," Proc Natl Acad Sci U S A. 91(24):11422-11426 (1994).
Evans et al., "Design of nonpeptidal ligands for a peptide receptor: Cholecystokinin antagonists," J Med Chem. 30(7):1229-1239 (1987).
Fauchere et al., "Association with HeLa cells of campylobacter jejuni and campylobacter coli isolated from human feces," Infect Immun. 54(2):283-287 (1986).
Fioretti et al., "Aprotinin-like isoinhibitors in bovine organs," Biol Chem Hoppe Seyler. 369 Suppl:37-42 (1988).
Fodor et al., "Multiplexed biochemical assays with biological chips," Nature. 364(6437):555-556 (1993).
Furuta et al., "Structure-antinociceptive activity studies with neurotensin," Br J Pharmacol. 83(1):43-48 (1984).
Gabathuler, "Approaches to transport therapeutic drugs across the blood-brain barrier to treat brain diseases," Neurobiol Dis. 37(1):48-57 (2010).
Gallop et al., "Applications of combinatorial technologies to drug discovery. 1. Background and peptide combinatorial libraries," J Med Chem. 37(9):1233-1251 (1994).
Halab et al., "Design, synthesis, and conformational analysis of azacycloalkane amino acids as conformationally constrained probes for mimicry of peptide secondary structures," Biopolymers. 55(2):101-122 (2000).
Hanessian et al., "Synthesis of (4$S$)-hydroxymethyl-(2$R$)-(2-propyl)-butyrolactone: A quest for a practical route to an important hydroxyethylene isostere chiron," Tetrahedron. 53(18):6281-6294 (1997).
Hein et al., "Click chemistry, a powerful tool for pharmaceutical sciences," Pharm Res. 25(10):2216-2230 (2008).
Hijova, Matrix metalloproteinases: their biological functions and clinical implications, Bratisl Lek Listy. 106(3):127-132 (2005).
Hiraoka et al., "Matrix metalloproteinases regulate neovascularization by acting as pericellular fibrinolysins," Cell. 95(3):365-377 (1998).
Hong et al., "Coexpression of cyclooxygenase-2 and matrix metalloproteinases in human aortic atherosclerotic lesions," Yonsei Med J. 41(1):82-88 (2000).
Hotary et al., "Membrane type I matrix metalloproteinase usurps tumor growth control imposed by the three-dimensional extracellular matrix," Cell. 114(1):33-45 (2003).
Huang et al., "Production of bioactive human beta-defensin 5 and 6 in *Escherichia coli* by soluble fusion expression," Protein Expr Purif. 61(2):168-174 (2008).
Hudson et al., "Methionine enkephalin and isosteric analogues. I. Synthesis on a phenolic resin support," Int J Pept Protein Res. 14(3):177-185 (1979).
Imai et al., "Expression of membrane-type 1 matrix metalloproteinase and activation of progelatinase A in human osteoarthritic cartilage," Am J Pathol. 151(1):245-256 (1997).
Itoh et al., "MT1-MMP: a potent modifier of pericellular microenvironment," J Cell Physiol. 206(1):1-8 (2006).
Jameson et al., "A rationally designed CD4 analogue inhibits experimental allergic encephalomyelitis," Nature. 368(6473):744-746 (1994).
Kajita et al., "Membrane-type 1 matrix metalloproteinase cleaves CD44 and promotes cell migration" J Cell Biol. 153(5):893-904 (2001).
Kamps et al., "Uptake of long-circulating immunoliposomes, directed against colon adenocarcinoma cells, by liver metastases of colon cancer," J Drug Target. 8(4):235-245 (2000).
Kesari et al., "Phase II study of temozolomide, thalidomide, and celecoxib for newly diagnosed glioblastoma in adults," Neuro Oncol. 10(3):300-308 (2008).

(56) References Cited

OTHER PUBLICATIONS

Kirpotin et al., "Sterically stabilized anti-HER2 immunoliposomes: design and targeting to human breast cancer cells in vitro," Biochemistry. 36(1):66-75 (1997).
Konttinen et al., "Analysis of 16 different matrix metalloproteinases (MMP-1 to MMP-20) in the synovial membrane: different profiles in trauma and rheumatoid arthritis" Ann Rheum Dis. 58(11):691-7 (1999).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", Euro J of Cancer. 6(12):133, Abstract 424 (2008).
Kurzrock et al., "ANG1005: Results of a Phase I study in patients with advanced solid tumors and metastatic brain cancer," Poster B168, ACCR/NCL/EORTC Annual Meeting (2009) (2 pages).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012).
Lam et al., A new type of synthetic peptide library for identifying ligand-binding activity, Nature. 354(6348):82-4 (1991).
Lam, "Application of combinatorial library methods in cancer research and drug discovery," Anticancer Drug Des. 12(3):145-67 (1997).
Langer, "New methods of drug delivery," Science. 249(4976):1527-33 (1990).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Markman et al., "Phase II trial of weekly single-agent paclitaxel in platinum/paclitaxel-refractory ovarian cancer," J Clin Oncol. 20(9):2365-9 (2002).
Martinez-Fong et al., "Neurotensin-SPDP-poly-L-lysine conjugate: a nonviral vector for targeted gene delivery to neural cells," Molecular Brain Research 69:249-262 (1999).
Michaud et al., "Risks and benefits of taxanes in breast and ovarian cancer," Drug Saf. 23(5):401-28 (2000).
Moase et al., "Anti-MUC-1 immunoliposomal doxorubicin in the treatment of murine models of metastatic breast cancer," Biochim Biophys Acta. 1510(1-2):43-55 (2001).
Nakada et al., "Expression and tissue localization of membrane-type 1, 2, and 3 matrix metalloproteinases in human astrocytic tumors," Am J Pathol. 154(2):417-28 (1999).
Nam et al., "Sterically stabilized anti-G(M3), anti-Le(x) immunoliposomes: targeting to B16BL6, HRT-18 cancer cells," Oncol Res. 11(1):9-16 (1999).
Nyalendo et al., "Impaired tyrosine phosphorylation of membrane type 1-matrix metalloproteinase reduces tumor cell proliferation in three-dimensional matrices and abrogates tumor growth in mice," Carcinogenesis. 29(8):1655-64 (2008).
Nyalendo et al., "Src-dependent phosphorylation of membrane type I matrix metalloproteinase on cytoplasmic tyrosine 573: role in endothelial and tumor cell migration," J Biol Chem. 282(21):15690-9 (2007).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Vector-mediated drug delivery to the brain," Adv Drug Deliv Rev. 36(2-3):299-321 (1999).
Park et al., "Development of anti-p185HER2 immunoliposomes for cancer therapy," Proc Natl Aced Sci U S A. 92(5):1327-31 (1995).
Park et al., "Recombinant expression of biologically active rat leptin in *Escherichia coli*," Protein Expr Purif. 22(1):60-69 (2001).
Pathan et al. "CNS drug delivery systems: novel approaches," Recent Pat Drug Deliv Formul. 3(1):71-89 (2009).
Pei et al., "Transmembrane-deletion mutants of the membrane-type matrix metalloproteinase-1 process progelatinase A and express intrinsic matrix-degrading activity," J Biol Chem. 271(15):9135-9140 (1996).
Powell et al., "Peptide stability in drug development. II. Effect of single amino acid substitution and glycosylation on peptide reactivity in human serum," Pharm Res. 10(9):1268-73 (1993).
Rajavashisth et al., "Membrane type 1 matrix metalloproteinase expression in human atherosclerotic plaques: evidence for activation by proinflammatory mediators," Circulation. 99(24):3103-9 (1999).
Rizo et al. "Constrained peptides: models of bioactive peptides and protein substructures," Annu Rev Biochem. 61:387-418 (1992).
Rose et al., "Metastatic patterns in histologic variants of ovarian cancer. An autopsy study," Cancer. 64(7):1508-13 (1989).
Rudikoff et al., "Single amino acid substitution altering antigen-binding specificity," Proc Natl Acad Sci USA. 79:1979-83 (1982).
Sabeh et al. "Tumor cell traffic through the extracellular matrix is controlled by the membrane-anchored collagenase MT1-MMP," J Cell Biol. 167(4):769-81 (2004).
Sahm et al. "Receptor binding affinities and biological activities of linear and cyclic melanocortins in B16 murine melanoma cells expressing the native MC1 receptor," J Pharm Pharmacol. 48(2):197-200 (1996).
Scott et al. "Searching for peptide ligands with an epitope library," Science. 249(4967):386-90 (1990).
Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Shao et al., "Angiopep-2 modified PE-PEG based polymeric micelles for amphotericin B delivery targeted to the brain," J Control Release. 147(1):118-26 (2010).
Spatola et al., "Structure-activity relationships of enkephalins containing serially replaced thiomethylene amide bond surrogates," Life Sci. 38(14):1243-9 (1986).
Svenson et al., "Dendrimers in biomedical applications—reflections on the field," Adv Drug Deliv Rev. 57(15):2106-2129 (2005).
Tilstra et al., "Protein transduction: identification, characterization and optimization," *Biochem Soc Trans*. 35(4):811-815 (2007).
UniProt Consortium, "P08183 (MDR1_HUMAN)," <http://www.uniprot.org/uniprot/P08183>, retrieved on Sep. 18, 2013 (16 pages).
Vincent, "Neurotensin receptors: binding properties, transduction pathways, and structure," Cell Mol Neurobiol. 15(5):501-512 (1995).
Wang et al., "Polyamidoamine dendrimers with a modified Pentaerythritol core having high efficiency and low cytotoxicity as gene carriers," Biomacromolecules. 10(3):617-622 (2009).
Wang et al., "Synthesis and antinociceptive effects of endomorphin-1 analogs with C-terminal linked by oligoarginine," Peptides. 32(2):293-9 (2011).
Williamson et al., "Expression and purification of recombinant neurotensin in *Escherichia coli*," Protein Expr Purif. 19(2):271-5 (2000).
Yano et al., "Simultaneous activation of two different receptor systems by enkephalin/neurotensin conjugates having spacer chains of various lengths," Eur J Pharm Sci. 7:41-48 (1998).
Zhai et al. "Expression of membrane type 1 matrix metalloproteinase is associated with cervical carcinoma progression and invasion," Cancer Res. 65(15):6543-6550 (2005).
Zhang et al. "In vitro gene delivery using polyamidoamine dendrimers with a trimesyl core," Biomacromolecules. 6(1):341-350 (2005).

* cited by examiner $V_D$ for aprotinin in brain parenchyma = 3 μl/100 g

FIG. 17 Alignement between aprotinin and three human proteins with a similar domain

SEQUENCE LISTING

```
<160> NUMBER OF SEQ ID NOS: 9

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Arg Ala Lys Arg Asn Asn Phe Lys Ser Ala
1               5                   10

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Arg Pro Asp Phe Cys Leu Glu Pro Pro Tyr Thr Gly Pro Cys Val
1               5                   10                  15

Ala Arg Ile Ile Arg
            20
```

```
<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Leu Cys Gln Thr Phe Val Tyr Gly Gly Cys Arg Ala Lys Arg Asn
1               5                   10                  15

Asn Phe Lys Ser Ala Glu
            20

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Phe Phe Tyr Gly Gly Cys Arg Gly Lys Arg Asn Asn Phe Lys Thr
1               5                   10                  15

Glu Glu Tyr

<210> SEQ ID NO 5
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
        50                  55

<210> SEQ ID NO 6
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Pro Pro Tyr Thr Gly Pro Cys Lys Ala Arg Ile Ile Arg Tyr Phe
1               5                   10                  15

Tyr Asn Ala Lys Ala Gly Leu Cys Gln Thr Phe Val Tyr Gly Gly Cys
            20                  25                  30

Arg Ala Lys Arg Asn Asn Phe Lys Ser Ala Glu Asp Ser Met Arg Thr
        35                  40                  45

Cys Gly Gly Ala
    50
```

```
<210> SEQ ID NO 7
<211> LENGTH: 56
<212> TYPE: PRT
<213> ORGANISM: Homo sapiens

<400> SEQUENCE: 7

Leu Gly Tyr Ser Ala Gly Pro Cys Met Gly Met Thr Ser Arg Tyr Phe
1               5                   10                  15

Tyr Asn Gly Thr Ser Met Ala Cys Glu Thr Phe Gln Tyr Gly Gly Cys
                20                  25                  30

Met Gly Asn Gly Asn Asn Phe Val Thr Glu Lys Glu Cys Leu Gln Thr
            35                  40                  45

Cys Arg Thr Val Ala Ala Cys Asn
    50                  55

<210> SEQ ID NO 8
<211> LENGTH: 60
<212> TYPE: PRT
<213> ORGANISM: Homo sapiens

<400> SEQUENCE: 8

Glu Gln Ala Glu Thr Gly Pro Cys Arg Ala Met Ile Ser Arg Trp Tyr
1               5                   10                  15

Phe Asp Val Thr Glu Gly Lys Cys Ala Pro Phe Phe Tyr Gly Gly Cys
                20                  25                  30

Gly Gly Asn Arg Asn Asn Phe Asp Thr Glu Glu Tyr Cys Met Ala Val
            35                  40                  45

Cys Gly Ser Ala Met Ser Gln Ser Leu Leu Lys Thr
    50                  55                  60

<210> SEQ ID NO 9
<211> LENGTH: 58
<212> TYPE: PRT
<213> ORGANISM: Homo sapiens

<400> SEQUENCE: 9

Ala Ser Asn Lys Val Gly Arg Cys Arg Gly Ser Phe Pro Arg Trp Tyr
1               5                   10                  15

Tyr Asp Pro Thr Glu Gln Ile Cys Lys Ser Phe Val Tyr Gly Gly Cys
                20                  25                  30

Leu Gly Asn Lys Asn Asn Tyr Leu Arg Glu Glu Cys Ile Leu Ala
            35                  40                  45

Cys Arg Gly Val Gln Gly Pro Ser Met Glu
    50                  55
```

METHOD FOR TRANSPORTING A COMPOUND ACROSS THE BLOOD-BRAIN BARRIER

CROSS-REFERENCE TO RELATED APPLICATIONS

This application is the national phase of International (PCT) Patent Application Serial No. PCT/CA04/000011, filed Jan. 5, 2004, published under PCT Article 21(2) in English, which claims priority to and the benefit of U.S. Provisional Patent Application Serial No. 60/437,986, filed Jan. 6, 2003, the disclosures of which are incorporated herein by reference.

TECHNICAL FIELD

The present invention relates to improvements in the field of drug delivery. More particularly, the invention relates to a non-invasive and flexible method and carrier for transporting a compound or drug across the blood-brain barrier of an individual.

BACKGROUND OF THE INVENTION

In the development of a new therapy for brain pathologies, the blood-brain barrier (BBB) is considered as a major obstacle for the potential use of drugs for treating disorders of the central nervous system (CNS). The global market for CNS drugs was $33 billion in 1998, which was roughly half that of global market for cardiovascular drugs, even though in the United States, nearly twice as many people suffer from CNS disorders as from cardiovascular diseases. The reason for this lopsidedness is that more than 98% of all potential CNS drugs do not cross the blood-brain barrier. In addition, more than 99% of worldwide CNS drug development is devoted solely to CNS drug discovery, and less than 1% is directed to CNS drug delivery. This ratio could justify why no efficient treatment is currently available for the major neurological diseases such as brain tumors, Alzheimer's and stroke.

The brain is shielded against potentially toxic substances by the presence of two barrier systems: the blood-brain barrier (BBB) and the blood-cerebrospinal fluid barrier (BCSFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS. As a general rule, only lipophilic molecules smaller than about 500 Daltons can pass across the BBB, i.e., from blood to brain. However, the size of many drugs that show promising results in animal studies for treating CNS disorders is considerably bigger. Thus, peptide and protein therapeutics are generally excluded from transport from blood to brain, owing to the negligible permeability of the brain capillary endothelial wall to these drugs. Brain capillary endothelial cells (BCECs) are closely sealed by tight junctions, possess few fenestrae and few endocytic vesicles as compared to capillaries of other organs. BCECs are surrounded by extracellular matrix, astrocytes, pericytes and microglial cells. The close association of endothelial cells with the astrocyte foot processes and the basement membrane of capillaries are important for the development and maintenance of the BBB properties that permit tight control of blood-brain exchange.

To date, there is no efficient drug delivery approach available for the brain. The methods under investigation for peptide and protein drug delivery to the brain may be divided in three principal strategies. Firstly, invasive procedures include the direct intraventricular administration of drugs by means of surgery, and the temporary disruption of the BBB via intracarotid infusion of hyperosmolar solutions. Secondly, the pharmacologically-based strategy consists in facilitating the passage through the BBB by increasing the lipid solubility of peptides or proteins. Thirdly, physiologic-based strategies exploit the various carrier mechanisms at the BBB, which have been characterized in the recent years. In this approach, drugs are attached to a protein vector that performs like receptors-targeted delivery vehicle on the BBB. This approach is highly specific and presents high efficacy with an extreme flexibility for clinical indications with unlimited targets. In the present invention, the latter approach has been investigated.

It would be highly desirable to be provided with an improvement in the field of drug delivery.

It would also be highly desirable to be provided with a non-invasive and flexible method and a carrier for transporting a compound or drug across the BBB of an individual.

SUMMARY OF THE INVENTION

One aim of the present invention is to provide an improvement in the field of drug delivery.

Another aim of the present invention is to provide a non-invasive and flexible method and carrier for transporting a compound or drug across the blood-brain barrier of an individual.

According to one embodiment of the invention, there is provided a method for transporting an agent across the blood-brain barrier of a patient, which comprises the step of administering to the patient a compound comprising the agent attached to aprotinin, a pharmaceutically acceptable salt of aprotinin, a fragment of aprotinin or a pharmaceutically acceptable salt of a fragment of aprotinin.

According to a further embodiment of the invention, there is provided a use of aprotinin, a pharmaceutically acceptable salt of aprotinin, a fragment of aprotinin or a pharmaceutically acceptable salt of a fragment of aprotinin for transporting a compound attached thereto across the blood-brain barrier of a patient.

According to another embodiment of the invention, there is provided a use of aprotinin, a pharmaceutically acceptable salt of aprotinin, a fragment of aprotinin or a pharmaceutically acceptable salt of a fragment of aprotinin in the manufacture of a medicament for treating a neurological disease across the blood-brain barrier of a patient.

According to yet another embodiment of the invention, there is provided a use of aprotinin, a pharmaceutically acceptable salt of aprotinin, a fragment of aprotinin or a pharmaceutically acceptable salt of a fragment of aprotinin in the manufacture of a medicament for treating a central nervous system disorder across the blood-brain barrier of a patient.

According to another embodiment of the invention, there is provided compounds of formula R-L-M or pharmaceutically acceptable salts thereof, wherein R is aprotinin or a fragment thereof, L is a linker or a bond and M is an agent or a drug selected from the group consisting of a small molecule drug, a protein, a peptide and an enzyme.

According to another embodiment of the invention, there is provided a method for treating a neurological disease of a patient comprising administering to the patient a medicament comprising aprotinin, a pharmaceutically acceptable salt of aprotinin, a fragment of aprotinin or a pharmaceutically acceptable salt of a fragment of aprotinin, and a compound adapted to treat the disease, the compound being attached to the aprotinin.

According to a further embodiment of the invention, there is provided a method for treating a central nervous system disorder of a patient comprising administering to the patient a medicament comprising aprotinin, a pharmaceutically acceptable salt of aprotinin, a fragment of aprotinin or a pharmaceutically acceptable salt of a fragment of aprotinin, and a compound adapted to treat the disease, the compound being attached to the aprotinin.

In accordance with one embodiment of the present invention, there is provided a carrier for transporting an agent attached thereto across a blood-brain barrier, wherein the carrier is able to cross the blood-brain barrier after attachment to the agent and thereby transport the agent across the blood-brain barrier.

In a preferred embodiment of the present invention, the transporting does not affect blood-brain barrier integrity.

In a preferred embodiment of the present invention, the carrier is selected from the group consisting of aprotinin, a functional derivative of aprotinin, Angio-pep1 and a functional derivative of Angio-pep1.

In a preferred embodiment of the present invention, the agent is selected from the group consisting of a drug, a medicine, a protein, a peptide, an enzyme, an antibiotic, an anticancer agent, a molecule active at the level of the central nervous system, a radioimaging agent, an antibody, a cellular toxin, a detectable label and an anti-angiogenic compound.

In a preferred embodiment of the present invention, the anti-cancer agent is Paclitaxel.

In a preferred embodiment of the present invention, the detectable label is selected from the group consisting of a radioactive label, a green fluorescent protein, a histag protein and β-galactosidase.

In a preferred embodiment of the present invention, the agent has a maximum molecular weight of 160,000 Daltons.

In a preferred embodiment of the present invention, the transporting is effected by receptor-mediated transcytosis or adsorptive-mediated transcytosis.

In a preferred embodiment of the present invention, the agent is for treatment of a neurological disease.

In a preferred embodiment of the present invention, the neurological disease is selected from the group consisting of a brain tumor, a brain metastasis, schizophrenia, epilepsy, Alzheimer's disease, Parkinson's disease, Huntington's disease, stroke and blood-brain barrier related malfunctions.

In a preferred embodiment of the present invention, the blood-brain barrier related malfunction disease is obesity.

In a preferred embodiment of the present invention, the transporting results in delivery of the agent to the central nervous system (CNS) of an individual.

In a preferred embodiment of the present invention, the agent is releasable from the carrier after transport across the blood-brain barrier.

In a preferred embodiment of the present invention, the agent is released from the carrier after transport across the blood-brain barrier.

In a preferred embodiment of the present invention, there is provided a pharmaceutical composition for transporting an agent across a blood-brain barrier, the composition comprising a carrier according to an embodiment of the present invention in association with a pharmaceutically acceptable excipient.

In accordance with another embodiment of the present invention, there is provided a pharmaceutical composition for treating a neurological disease comprising a carrier according to an embodiment of the present invention in association with a pharmaceutically acceptable excipient.

In accordance with another embodiment of the present invention, there is provided a pharmaceutical composition for delivery of an agent to the CNS of an individual, the composition comprising a carrier according to an embodiment of the present invention in association with a pharmaceutically acceptable excipient.

In accordance with another embodiment of the present invention, there is provided a conjugate for transporting an agent across a blood-brain barrier, the conjugate comprising: (a) a carrier; and (b) an agent attached to the carrier, wherein the conjugate is able to cross the blood-brain barrier and thereby transport the agent across the blood-brain barrier.

In accordance with another embodiment of the present invention, there is provided a pharmaceutical composition for transporting an agent across a blood-brain barrier, the composition comprising a conjugate according to an embodiment of the present invention in association with a pharmaceutically acceptable excipient.

In accordance with an embodiment of the present invention, there is provided a pharmaceutical composition for treating a neurological disease, the composition comprising a conjugate according to an embodiment of the present invention in association with a pharmaceutically acceptable excipient.

In accordance with another embodiment of the present invention, there is provided a pharmaceutical composition for delivery of an agent to the CNS of an individual, the composition comprising a conjugate according to an embodiment of the present invention in association with a pharmaceutically acceptable excipient.

In accordance with another embodiment of the present invention, there is provided a use of a carrier for transporting an agent attached thereto across a blood-brain barrier in the manufacture of a medicament for transporting the agent across the blood-brain barrier.

In accordance with another embodiment of the present invention, there is provided a pharmaceutical composition for transporting an agent across a blood-brain barrier, the composition comprising a medicament manufactured as defined in an embodiment of the present invention in association with a pharmaceutically acceptable excipient.

In accordance with another embodiment of the present invention, there is provided a use of a carrier for transporting an agent attached thereto across a blood-brain barrier in the manufacture of a medicament for treating a neurological disease in an individual.

In accordance with another embodiment of the present invention, there is provided a pharmaceutical composition for treating a neurological disease comprising a medicament manufactured as defined in an embodiment of the present invention in association with a pharmaceutically acceptable excipient.

In accordance with another embodiment of the present invention, there is provided a use of a carrier for transporting an agent attached thereto across a blood-brain barrier in the manufacture of a medicament for treating a central nervous system disorder in an individual.

In accordance with another embodiment of the present invention, there is provided a pharmaceutical composition for treating a central nervous system disorder, the composition comprising a medicament manufactured as defined in an embodiment of the present invention in association with a pharmaceutically acceptable excipient.

In accordance with another embodiment of the present invention there is provided a conjugate of formula R-L-M or a pharmaceutically acceptable salt thereof, wherein R is a carrier able to cross the blood-brain barrier after attachment to L-M and thereby transport M across the blood-brain barrier, L is a linker or a chemical bond and M is an agent selected from the group consisting of a drug, a medicine, a protein, a peptide, an enzyme, an antibiotic, an anti-cancer agent, a molecule active at the level of the central nervous system, a radioimaging agent, an antibody, a cellular toxin, a detectable label and an anti-angiogenic compound.

In accordance with another embodiment of the present invention, there is provided a use of a conjugate according to an embodiment of the present invention for transporting an agent attached thereto across a blood-brain barrier.

In accordance with another embodiment of the present invention, there is provided a use of a conjugate according to an embodiment of the present invention for treating a neurological disease in an individual.

In accordance with another embodiment of the present invention, there is provided a use of a conjugate according to an embodiment of the present invention for treating a central nervous system disorder in an individual.

In accordance with another embodiment of the present invention, there is provided a method for transporting an agent across a blood-brain barrier, which comprises the step of administering to an individual a pharmaceutical composition according to an embodiment of the present invention.

In a preferred method of the present invention the pharmaceutical composition is administered to the individual intra-arterially, intra-nasally, intra-peritoneally, intravenously, intramuscularly, sub-cutaneously, transdermally or per os.

In accordance with another embodiment of the present invention, there is provided a method for treating a neurological disease in an individual comprising administering to the individual in need thereof a therapeutically effective amount of a pharmaceutical composition according to an embodiment of the present invention.

In accordance with another embodiment of the present invention, there is provided a method for treating a central nervous system disorder in an individual comprising administering to the individual in need thereof a therapeutically effective amount of a pharmaceutical composition according to an embodiment of the present invention.

For the purpose of the present invention the following terms are defined below.

The term "carrier" or "vector" is intended to mean a compound or molecule that is able to cross the blood-brain barrier and be attached to or conjugated to another compound or agent and thereby be able to transport the other compound or agent across the blood-brain barrier. For example, the carrier may bind to receptors present on brain endothelial cells and thereby be transported across the blood-brain barrier by transcytosis. Preferably the carrier is a protein or molecule for which very high levels of transendothelial transport are obtained without any effects on the blood-brain barrier integrity. The carrier may be, but is not limited to, a protein, a peptide, or a peptidomimetic and can be naturally occurring or produced by chemical synthesis or recombinant genetic technology (genetic engineering).

The term "carrier-agent conjugate" is intended to mean a conjugate of a carrier and another compound or agent. The conjugation can be chemical in nature, such as with a linker, or genetic in nature for example by recombinant genetic technology, such as in a fusion protein with for example green fluorescent protein, β-galactosidase or Histag protein.

The expression "small molecule drug" is intended to mean a drug having a molecular weight of 1000 g/mol or less.

The terms "treatment", "treating" and the like are intended to mean obtaining a desired pharmacologic and/or physiologic effect, e.g., inhibition of cancer cell growth, death of a cancer cell or amelioration of a neurological disease or condition. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing cancer) from occurring in an individual who may be predisposed to the disease but has not yet been diagnosed as having it; (b) inhibiting a disease, (e.g., arresting its development); or (c) relieving a disease (e.g., reducing symptoms associated with a disease). "Treatment" as used herein covers any administration of a pharmaceutical agent or compound to an individual to treat, cure, alleviate, improve, diminish or inhibit a condition in the individual, including, without limitation, administering a carrier-agent conjugate to an individual.

The term "cancer" is intended to mean any cellular malignancy whose unique trait is the loss of normal controls which results in unregulated growth, lack of differentiation and ability to invade local tissues and metastasize. Cancer can develop in any tissue of any organ. More specifically, cancer is intended to include, without limitation, cancer of the brain.

The term "administering" and "administration" is intended to mean a mode of delivery including, without limitation, intra-arterially, intra-nasally, intra-peritoneally, intravenously, intramuscularly, sub-cutaneously, transdermally or per os. The preferred one being per os. A daily dosage can be divided into one, two or more doses in a suitable form to be administered at one, two or more times throughout a time period.

The term "therapeutically effective" is intended to mean an amount of a compound sufficient to substantially improve some symptom associated with a disease or a medical condition. For example, in the treatment of cancer or a mental condition or neurological or CNS disease, an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

The carrier and carrier-agent conjugates of the present invention may be used in combination with either conventional methods of treatment and/or therapy or may be used separately from conventional methods of treatment and/or therapy.

When the carrier-agent conjugates of this invention are administered in combination therapies with other agents, they may be administered sequentially or concurrently to an individual. Alternatively, pharmaceutical compositions according to the present invention may be comprised of a combination of a carrier-agent conjugate of the present invention in association with a pharmaceutically acceptable excipient, as described herein, and another therapeutic or prophylactic agent known in the art.

It will be understood that a specific "effective amount" for any particular individual will depend upon a variety of factors including the activity of the specific agent employed, the age, body weight, general health, sex, and/or diet of the individual, time of administration, route of administration, rate of excretion, drug combination and the severity of the particular disease undergoing prevention or therapy.

Pharmaceutically acceptable acid addition salts may be prepared by methods known and used in the art.

As used herein, "pharmaceutically acceptable carrier" includes any and all solvents (such as phosphate buffered saline buffers, water, saline), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients can also be incorporated into the compositions.

The term "functional derivative" is intended to mean a "chemical derivative", "fragment", or "variant" biologically active sequence or portion of a carrier or agent or carrier-agent conjugate or a salt thereof of the present invention. A carrier functional derivative is able to be attached to or conjugated to another compound or agent and cross the blood-brain barrier and thereby be able to transport the other compound or agent across the blood-brain barrier.

The term "chemical derivative" is intended to mean a carrier, an agent, or a carrier-agent conjugate of the present invention, which contains additional chemical moieties not a part of the carrier, agent or carrier-agent conjugate. Covalent modifications are included within the scope of this invention. A chemical derivative may be conveniently prepared by direct chemical synthesis, using methods well known in the art. Such modifications may be, for example, introduced into a protein or peptide carrier, agent or carrier-agent conjugate by reacting targeted amino acid residues with an organic derivatizing agent that is capable of reacting with selected side chains or terminal residues. A carrier chemical derivative is able to cross the blood-brain barrier and be attached to or conjugated to another compound or agent and thereby be able to transport the other compound or agent across the blood-brain barrier. In a preferred embodiment, very high levels of transendothelial transport across the blood-brain barrier are obtained without any effects on the blood-brain barrier integrity.

The term "fragment" is intended to mean any piece or portion of a carrier, agent or carrier-agent conjugate. A fragment of a protein or peptide, for example, may be a subset of amino acids which makes up the sequence of the whole protein or peptide. A carrier fragment is able to be attached to or conjugated to another compound or agent and cross the blood-brain barrier and thereby be able to transport the other compound or agent across the blood-brain barrier.

The term "variant" is intended to mean to a carrier, agent or carrier-agent conjugate which is substantially similar to either the structure of a carrier, agent or carrier-agent conjugate, or any fragment thereof, of the present invention. A carrier variant is able to be attached to or conjugated to another compound or agent and cross the blood-brain barrier and thereby be able to transport the other compound or agent across the blood-brain barrier. Variant proteins, peptides, peptidomimetics and chemical structures of carriers of the present invention are contemplated.

The term "aprotinin fragment" is intended to mean a portion of aprotinin that can still transport a compound across the BBB. Such a fragment can comprise at least 12 amino acids, preferably at least 25 amino acids and more preferably at least 35 amino acids. Studies to determine the minimal sequence of aprotinin effective to interact with megalin have been performed by Hussain, M., Strickland, D. K., Bakillah, A., in The mammalian low-density lipoprotein receptor family. *Anno. Rev. Nutr.* 1999, 19, 141-172. For example, the minimal sequence for interaction of Aprotinin with Megalin receptor was determined to be CRAKRNNFKSA (SEQ ID NO:1). Accordingly, fragments comprising this minimal sequence are meant to be included by this term.

The term "agent" is intended to mean without distinction a drug or a compound such as a therapeutic agent or compound, a marker, a tracer or an imaging compound.

The term "therapeutic agent" or "agent" is intended to mean an agent and/or medicine and/or drug used to treat the symptoms of a disease, physical or mental condition, injury or infection and includes, but is not limited to, antibiotics, anti-cancer agents, anti-angiogenic agents and molecules active at the level of the central nervous system Paclitaxel, for example, can be administered intravenously to treat brain cancer.

The term "patient" or "individual treated" is intended to mean any one who receives a certain medical treatment, and includes being subjected to the administration of a carrier-agent or compound conjugate for detecting, tracing, marking or imaging a condition, such as a tumor. Preferably, the patient or individual treated is a mammal and more preferably a human.

The term "condition" is intended to mean any situation causing pain, discomfort, sickness, disease or disability (mental or physical) to or in an individual, including neurological disease, injury, infection, or chronic or acute pain. Neurological diseases which can be treated with the present invention include, but are not limited to, brain tumors, brain metastases, schizophrenia, epilepsy, Alzheimer's disease, Parkinson's disease, Huntington's disease and stroke.

DETAILED DESCRIPTION OF THE PREFERRED EMBODIMENT

Figure 1:
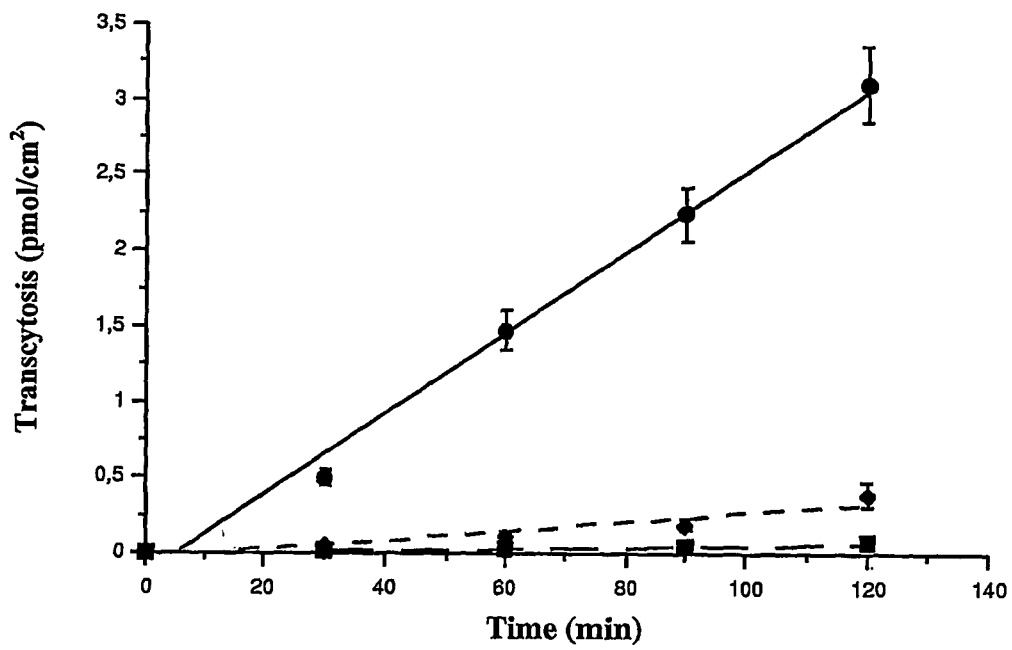
FIG. 1 is a plot showing the results of transcytosis experiments of aprotinin (●), p97 (♦), and ceruloplasmin (■) across bovine brain capillary endothelial cells (BBCECs)

The present invention relates to a new vector or carrier to transport an agent, medicine or other molecule to the brain and/or central nervous system (CNS). This carrier permits the passage of the agent, medicine or other molecule which is attached or coupled (conjugated) to the carrier and which are unable by themselves to cross the blood-brain barrier, to be transported across the blood-brain barrier. The carrier-conjugate can be a carrier-therapeutic agent conjugate. Such conjugates can be in the form of a composition, such as a pharmaceutical composition, for treatment of a condition or disease. This invention is based on the discovery that aprotinin binds to and crosses the brain capillary endothelial wall in a very effective manner. Aprotinin is known in the art to be a basic polypeptide that effectively inhibits a variety of serine proteases, including trypsin, chymotrypsin, kallikrein and pepsin. The transendothelial transport of aprotinin is approximately 10-50 times higher than that of other proteins including transferrin or ceruloplasmin. This high rate of passage is not caused by the disruption of the integrity of the blood-brain barrier since the permeability coefficient for sucrose is not affected by aprotinin.

This approach is very versatile since it permits conjugation of small as well as large molecules having very diverse therapeutic targets.

In accordance with the present invention a method for transporting an agent across the blood-brain barrier comprises administering to an individual an agent that comprises an active ingredient or a pharmaceutical agent attached to a carrier, such as aprotinin, or a functional derivative thereof.

In accordance with the present invention, the compound can be administered intra-arterially, intra-nasally, intra-peritoneally, intravenously, intramuscularly, sub-cutaneously, transdermally or per os to the patient. The agent is preferably an anti-angiogenic compound. The agent can have a maximum weight of 160,000 Daltons. Preferably, the agent is a marker or a drug such as a small molecule drug, a protein, a peptide or an enzyme. The drug preferably is adapted to treat a neurological disease or a central nervous system disorder of a patient. The drug can be a cytotoxic drug and the marker can be a detectable label such as a radioactive label, a green fluorescent protein, a histag protein or β-galactosidase. The agent is preferably delivered into the central nervous system of a patient.

According to still another preferred embodiment of the invention, the uses, methods, compounds, agents, drugs or medicaments of the invention do not alter the integrity of the blood-brain barrier of the patient.

According to a further preferred embodiment of the invention, aprotinin can be attached to an agent or a compound for transporting the agent or compound across the blood-brain barrier of a patient, the agent or compound being adapted to treat a neurological disease or to treat a central nervous system disorder.

The carrier or functional derivative thereof of the present invention or mixtures thereof may be linked to or labelled with a detectable label such as a radioimaging agent, such as those emitting radiation, for detection of a disease or condition, for example by the use of a radioimaging agent-antibody-carrier conjugate, wherein the antibody binds to a disease or condition-specific antigen. Other binding molecules besides antibodies and which are known and used in the art are also contemplated by the present invention. Alternatively, the carrier or functional derivative thereof of the present invention or mixtures thereof may be linked to a therapeutic agent, to treat a disease or condition, or may be linked to or labelled with mixtures thereof. Treatment is effected by administering a carrier-agent conjugate of the present invention to an individual under conditions which allow transport of the agent across the blood-brain barrier.

A therapeutic agent of the present invention can be a drug, a medicine, an agent emitting radiation, a cellular toxin (for example, a chemotherapeutic agent) and/or biologically active fragment thereof, and/or mixtures thereof to allow cell killing or it may be an agent to treat, cure, alleviate, improve, diminish or inhibit a disease or condition in an individual treated. A therapeutic agent can be a synthetic product or a product of fungal, bacterial or other microorganism, such as mycoplasma, viral etc., animal, such as reptile, or plant origin. A therapeutic agent and/or biologically active fragment thereof can be an enzymatically active agent and/or fragment thereof, or can act by inhibiting or blocking an important and/or essential cellular pathway or by competing with an important and/or essential naturally occurring cellular component.

Radioimaging agents emitting radiation (detectable radiolabels) for use in the present invention are exemplified by indium-111, technitium-99, or low dose iodine-131.

Detectable labels, or markers, for use in the present invention can be a radiolabel, a fluorescent label, a nuclear magnetic resonance active label, a luminescent label, a chromophore label, a positron emitting isotope for PET scanner, chemiluminescence label, or an enzymatic label. Fluorescent labels include, but are not limited to, green fluorescent protein (GFP), fluorescein, and rhodamine. Chemiluminescence labels include, but are not limited to, luciferase and β-galactosidase. Enzymatic labels include, but are not limited to peroxidase and phosphatase. A histag may also be a detectable label.

It is contemplated that an agent may be releasable from the carrier after transport across the blood-brain barrier, for example by enzymatic cleavage or breakage of a chemical bond between the carrier and the agent. The release agent would then function in its intended capacity in the absence of the carrier.

The present invention will be more readily understood by referring to the following examples which are given to illustrate the invention rather than to limit its scope.

Experimental Section

Determination of a Suitable Carrier

A reproducible blood-brain barrier in vitro model demonstrating in vivo characteristics has been used for screening assay and for mechanistic studies of drug transport to the brain. This efficient in vitro model of the blood-brain barrier was developed by the company CELLIAL™ Technologies was of prime importance to the reliable evaluation of the capacity of different carriers to reach the brain. The model consists of a co-culture of bovine brain capillary endothelial cells and rat glial cells. It presents ultrastructural features characteristic of brain endothelium including tight junctions, lack of fenestration, lack of transendothelial channels, low permeability for hydrophilic molecules and a high electrical resistance. Moreover, this model has shown a good correlation coefficient between in vitro and in vivo analysis of wide range of molecules tested. To date, all the data obtained show that this BBB model closely mimics the in vivo situation by reproducing some of the complexities of the cellular environment that exist in vivo, while retaining the experimental advantages associated with tissue culture. Thus, many studies have validated this cell co-culture as one of the most reproducible in vitro model of the BBB.

The in vitro model of BBB was established by using a co-culture of BBCECs and astrocytes. Prior to cell culture, plate inserts (Millicell-PC 3.0 μM; 30-mm diameter) were coated on the upper side with rat tail collagen. They were then set in six-well microplates containing the astrocytes and BBCECs were plated on the upper side of the filters in 2 mL of co-culture medium. This BBCEC medium was changed three times a week. Under these conditions, differentiated BBCECs formed a confluent monolayer 7 days later. Experiments were performed between 5 and 7 days after confluence was reached. The permeability coefficient for sucrose was measured to verify the endothelial permeability.

Primary cultures of mixed astrocytes were prepared from newborn rat cerebral cortex (Dehouck M. P., Meresse S., Delorme P., Fruchart J. C., Cecchelli, R. An Easier, Reproducible, and Mass-Production Method to Study the Blood-Brain Barrier In Vitro. *J. Neurochem*, 54, 1798-1801, 1990). Briefly, after removing the meninges, the brain tissue was forced gently through a 82 μm nylon sieve. Astrocytes were plated on six-well microplates at a concentration of $1.2 \times 10^5$ cells/mL in 2 mL of optimal culture medium (DMEM) supplemented with 10% heat inactivated fetal bovine serum. The medium was changed twice a week.

Bovine brain capillary endothelial cells (BBCECs) were obtained from Cellial Technologies. The cells were cultured in the presence of DMEM medium supplemented with 10% (v/v) horse serum and 10% heat-inactivated calf serum, 2 mM of glutamine, 50 μg/mL of gentamycin, and 1 ng/mL of basic fibroblast growth factor, added every other day.

Figure 2:
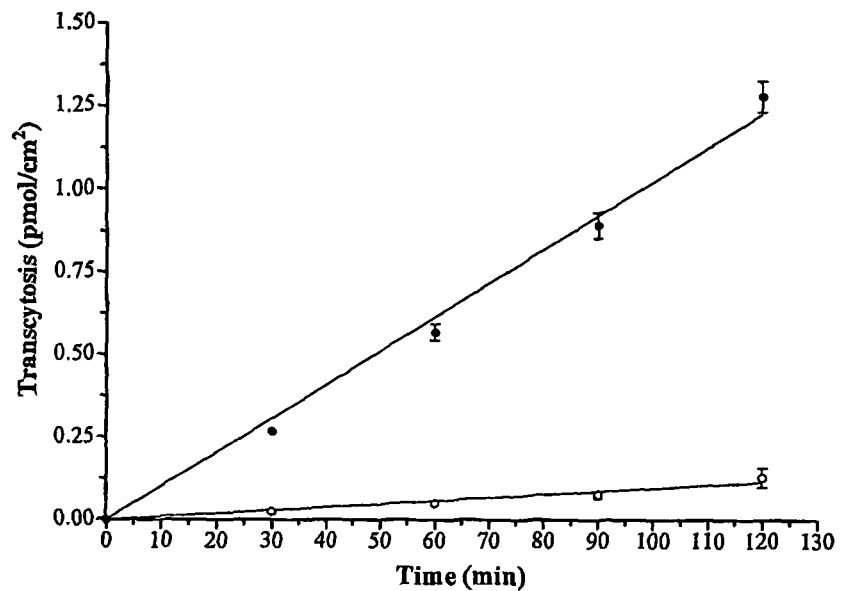
FIG. 2 is a plot showing the results of transcytosis experiments of aprotinin (●) and transferrin (○) across bovine brain capillary endothelial cells (BBCECs)
Figure 3:
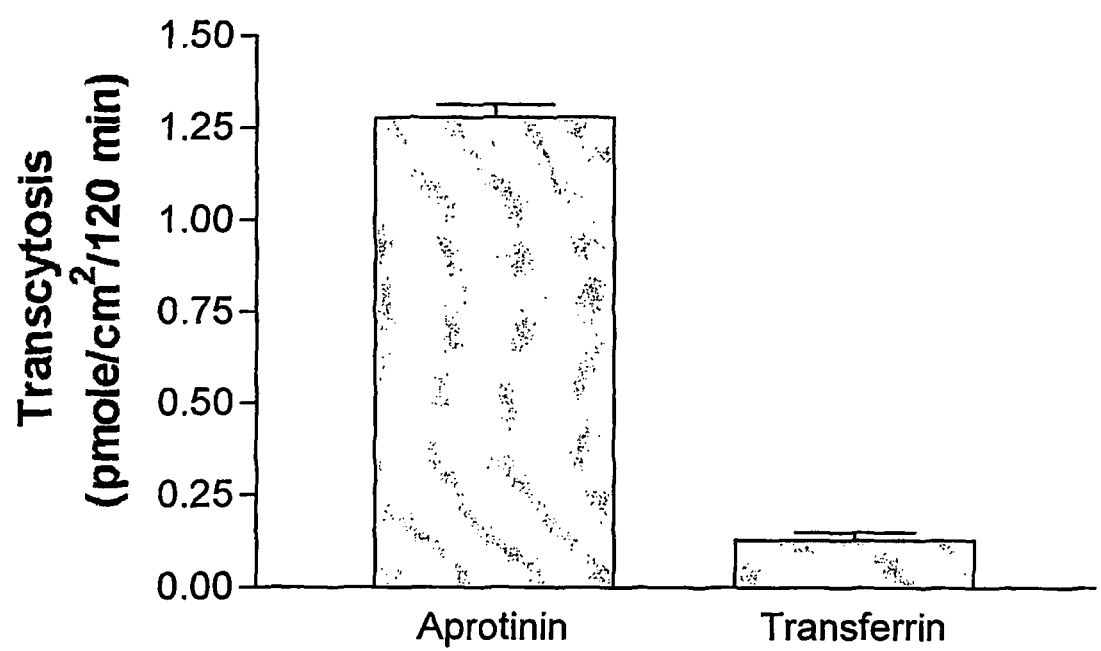
FIG. 3 is a bar graph illustrating that aprotinin has a higher transcytosis capacity than transferrin in a blood-brain barrier model.

In order to determine a suitable carrier for the present invention, tests have been performed using the in vitro model of the BBB. As illustrated in FIG. 1, transcytosis experiments of different proteins (aprotinin (●), p97 (♦) and ceruloplasmin (■)) across bovine brain capillary endothelial cells (BBCECs) were performed. FIGS. 2 and 3 show the results of transcytosis experiments performed with aprotinin (●) and transferrin (○) and using the same method than the experiments of FIG. 1. One insert covered with BBCECs was set into a six-well microplate with 2 mL of Ringer-Hepes and was pre-incubated for 2 h at 37° C. [$^{125}$I]-aprotinin, [$^{125}$I]-p97, [$^{125}$I]-ceruloplasmin or [$^{125}$I]-transferrin (250 nM final concentration) was added to the upper side of the filter covered with cells. At various times, the insert was transferred to another well to avoid a possible reendocytosis of [$^{125}$I]-proteins by the abluminal side of the BBCECs. At the end of experiment, [$^{125}$I]-proteins were assessed in 500 μL of the lower chamber of well by TCA precipitation. The results indicate that aprotinin has a higher transcytosis capacity than transferrin, p97 or ceruloplasmin in a blood-brain barrier model.

Aprotinin, p97 and bovine holo-transferrin were iodinated with standard procedures using iodo-beads from Sigma™. Bovine holo-transferrin was diluted in 0.1M phosphate buffer, pH 6.5 (PB). P97 obtained from Synapse Technologies in neutralized citrate at pH 7.0 was dialyzed against this PB. Two iodo-beads were used for each protein. These beads were washed twice with 3 mL of PB on a Whatman™ filter and resuspended in 60 μL of PB. $^{125}$I (1 mCi) from Amersham-Pharmacia biotech was added to the bead suspension for 5 minutes at room temperature. The iodination for each protein was initiated by the addition of 100 μg (80-100 μL). After an incubation of 10 minutes at room temperature, the supernatants were applied on a desalting column prepacked with 5 mL of cross-linked dextran from Pierce and $^{125}$I-proteins were eluted with 10 mL of PBS. Fractions of 0.5 mL were collected and the radioactivity in 5 μL of each fraction was measured. Fractions corresponding to $^{125}$I-proteins were pooled and dialyzed against Ringer-Hepes, pH 7.4. The efficiency of radiolabeling was between $0.6-1 \times 10^8$ cpm/100 μg of protein.

From FIGS. 1-3, it is clear that aprotinin has a transcytosis capacity which is quite higher than the other tested proteins. The data of FIGS. 1-3 have been summarized in Table 1, wherein a comparison of the different proteins has been made.

TABLE 1

Comparison of $^{125}$I-proteins (250 nM) transcytosis across BBCEC monolayers

| Proteins compared | Ratios (x-fold) |
|---|---|
| aprotinin/p97 | 8.2 |
| aprotinin/ceruloplasmin | 44.0 |
| aprotinin/transferrin | 11.6 |

Table 2 summarizes another experiment, wherein a comparison of additional different proteins has been made.

TABLE 2

Efficiency of aprotinin to cross the blood-brain barrier

| Proteins compared | Transcytosis (pmol/h/cm$^2$) | Ratios Aprotinin/Protein |
|---|---|---|
| Aprotinin | 2.7 | 1 |
| Melanotransferrin (p97) | 0.28 | 10 |
| Transferrin | 0.14 | 19 |
| Lactoferrin | 0.05 | 50 |
| Streptavidin | 0.09 | 30 |

In view of Tables 1 and 2, it can be seen that for aprotinin, a superior transendothelial transport was obtained in comparison with the other tested proteins and that the high transcytosis of aprotinin is from about 10 to 50-fold higher than these other proteins.

Aprotinin Integrity is not Affected by its Transcytosis across BBCEC Monolayers

Figure 4:
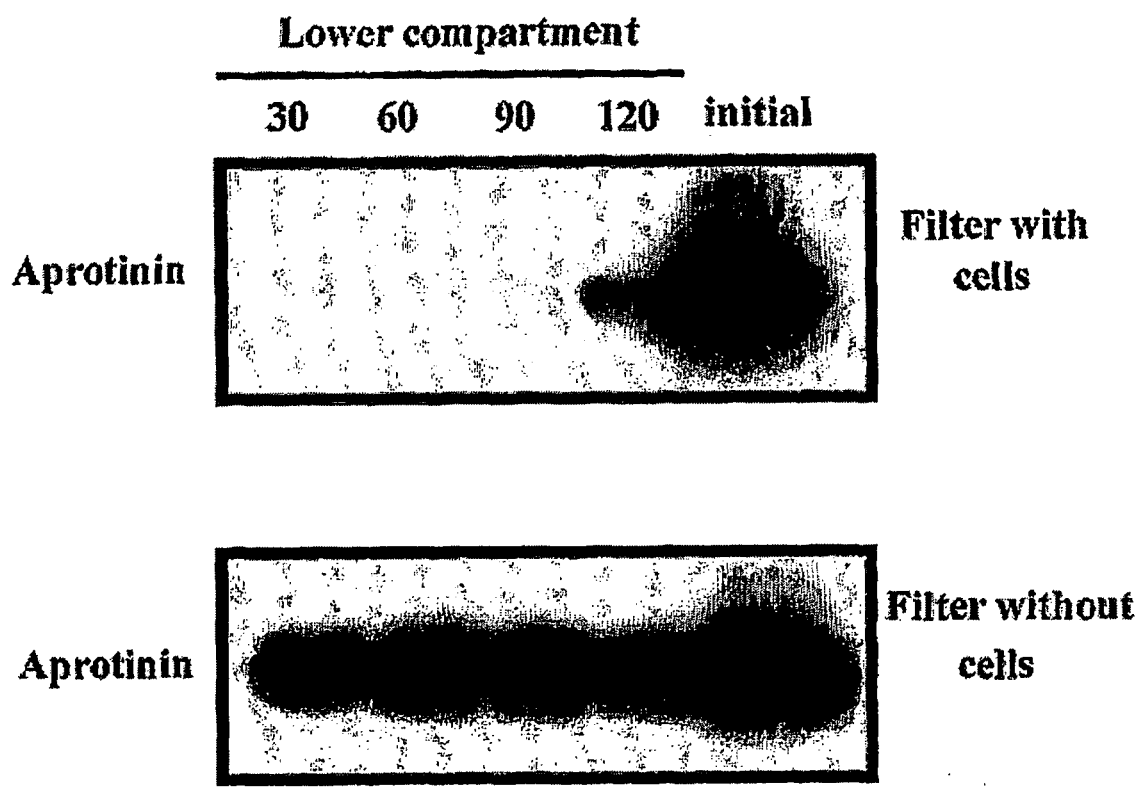
FIG. 4 is an SDS-PAGE analysis illustrating that aprotinin integrity is not affected by its transcytosis across BBCEC monolayers.

[$^{125}$I]-protein (0.5-1.5 μCi/assay) at a final concentration of 250 nM was added to the upper side of filters with or without BBCEC cells placed in 6-well plates. At each time point, filters were put in the next well of the 6-well plates. At the end of the experiment, aliquots were taken in each well and submitted to SDS-PAGE. Gels were then submitted to detection by autoradiography. The results, presented in FIG. 4, indicate that aprotinin integrity is not affected by its transcytosis across BBCEC monolayers.

Aprotinin does not affect the Blood-Brain Barrier Integrity

Figure 6:
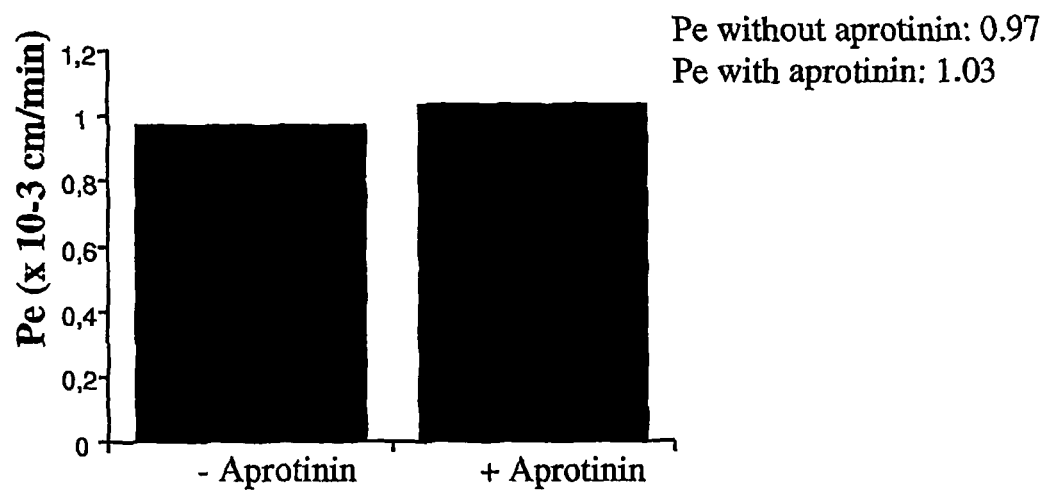
FIG. 6 is a graph showing the results of a sucrose permeability test of bovine brain capillary endothelial cells (BBCECs)

A further test was performed to determine the effect of aprotinin at 250 nM on the BBB integrity by measuring [$^{14}$C] sucrose permeability in the BBB model on BBCEC monolayers grown on filters in the presence of astrocytes. To achieve this test, brain endothelial cell monolayers grown on inserts were transferred to 6-well plates containing 2 mL of Ringer-Hepes per well (basolateral compartment) for two hours at 37° C. Ringer-Hepes solution was composed of 150 mM NaCl, 5.2 mM KCl, 2.2 mM CaCl$_2$, 0.2 mM MgCl$_2$, 6 mM NaHCO$_3$, 5 mM Hepes, 2.8 mM Hepes, pH 7.4. In each apical chamber, the culture medium was replaced by 1 mL Ringer-Hepes containing the labeled [$^{14}$C]-sucrose. At different times, inserts were placed into another well. [$^{14}$C] sucrose passage was measured at 37° C., on filters without cells (□) or with filters coated with BBCEC cells in the absence (Δ) or presence (○) of 5 μM aprotinin (FIG. 6). The results were plotted as the sucrose clearance (μl) as a function of time (min). The sucrose permeability coefficient was then determined. The permeability coefficient (Pe) was calculated as:

1) Clearance $(\mu l) = \frac{[C]A \times VA}{[C]L}$ wherein:

[C]A = Abluminal tracer concentration

VA = Volume of abluminal chamber

[C]L = Luminal tracer concentration

2) $1/Pe = (1/PSt - 1/PSf)/\text{filter area } (4.2 \text{ cm}^2)$

Figure 5:
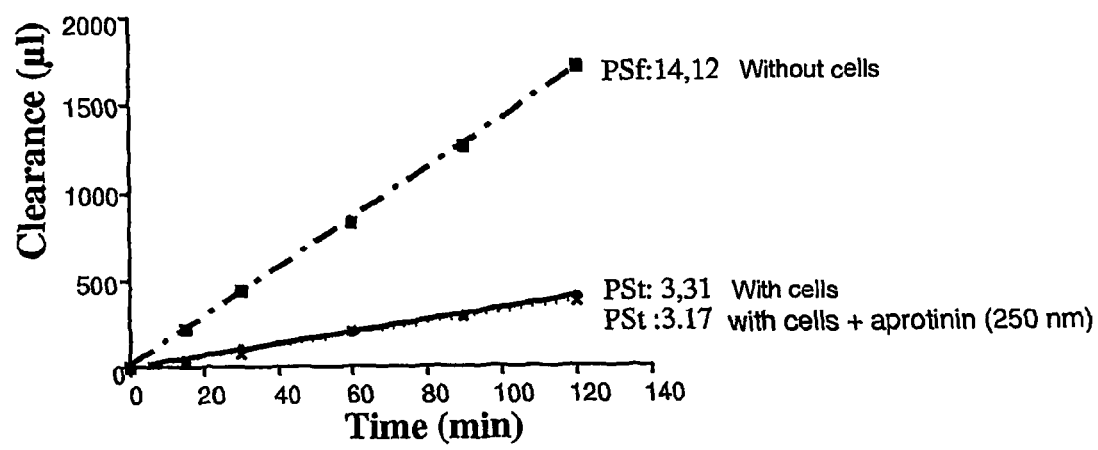
FIG. 5 is a plot of the clearance of [$^{14}$C]-sucrose expressed as a function of time. The clearance of sucrose was measured in the presence and the absence of 250 nM aprotinin.
Figure 7:
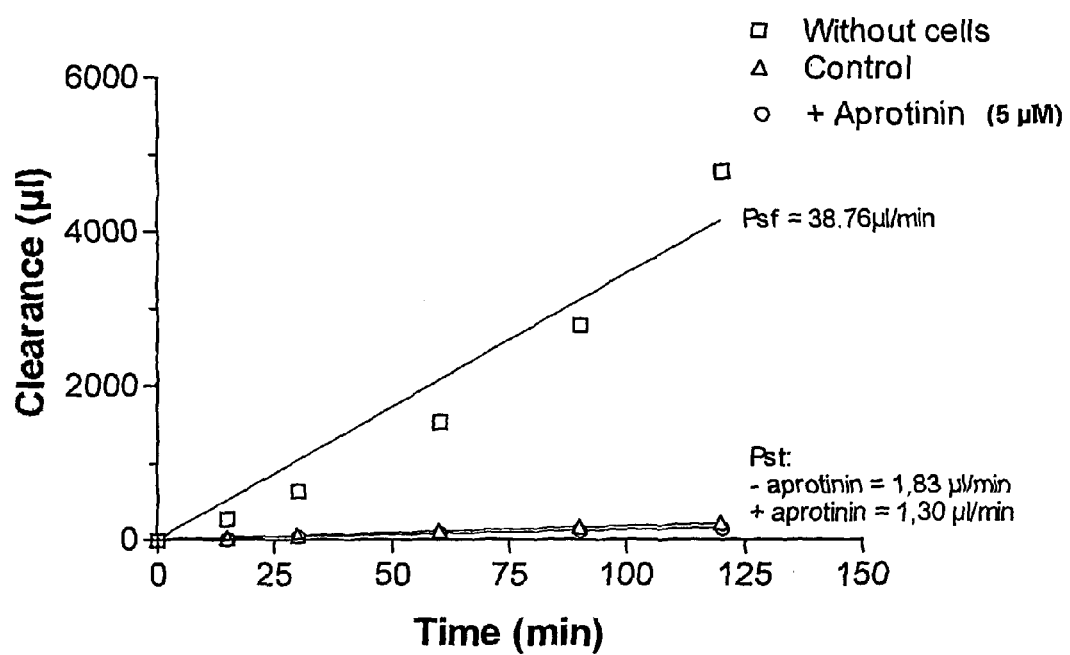
FIG. 7 is a plot of the clearance of [$^{14}$C]-sucrose expressed as a function of time illustrating that aprotinin does not affect blood-brain barrier integrity. The clearance of sucrose was measured in the presence and the absence of 5 µM aprotinin.

At the end of the experiments, amounts of the radiotracers in the basolateral compartment were measured in a liquid scintillation counter. The permeability coefficient (Pe) for sucrose was calculated as previously described (Dehouck, M. P., Jolliet-Riant, P., Brée, F., Fruchart, J. C., Cecchelli, R., Tillement, J. P., *J. Neurochem.* 58:1790-1797, 1992) using filters coated or non-coated with EC. The results of two experiments were plotted separately in terms of the clearance of [$^{14}$C]-sucrose (μL) as a function of time (min) (FIGS. 5 and 6). In FIGS. 5 and 6, PSt represents the permeability×surface area of a filter of the coculture and PSf represents the permeability of a filter coated with collagen and astrocytes plated on the bottom side of the filter B. The permeability coefficient (Pe) was calculated and it was demonstrated that the integrity of the BBB is not affected by aprotinin (see FIG. 6 for Pe calculated from FIG. 5, and Table 3 for Pe calculated from FIG. 7).

TABLE 3

Permeability coefficients of aprotinin demonstrate that aprotinin does not affect the integrity of the blood-brain barrier

| | Pe sucrose ($10^{-3}$ cm/min) |
|---|---|
| −Aprotinin | 0.46 ± 0.09 |
| +Aprotinin | 0.32 ± 0.04 |

Accumulation of [$^{125}$I]-Aprotinin in Human and Rat Capillaries

Figure 8:
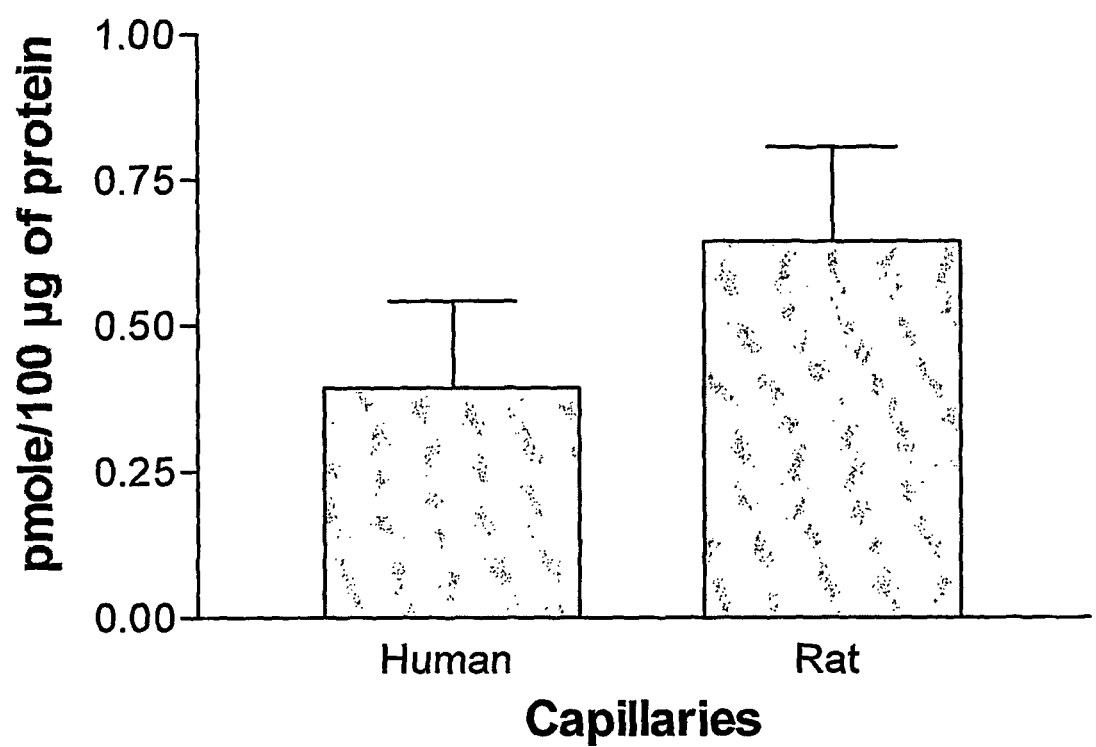
FIG. 8 is a bar graph illustrating the accumulation of [$^{125}$I]-aprotinin in human and rat capillaries.

Accumulation was measured at 37° C. for 1 hour. Incubation medium contained aprotinin at a final 100 nM concentration in Ringer/Hepes solution. Accumulation was stopped by addition of ice-cold stop-solution and filtration in vacuum through a 0.45 μM filter. Nonspecific binding of aprotinin to the capillaries surface was evaluated by the addition of the ice-cold solution before adding the incubation medium. This value was subtracted from accumulation value to obtain the real accumulation value. The results of this experiment are shown in FIG. 8.

Time-Course of Aprotinin Uptake in Human and Rat Capillaries

Figure 9:
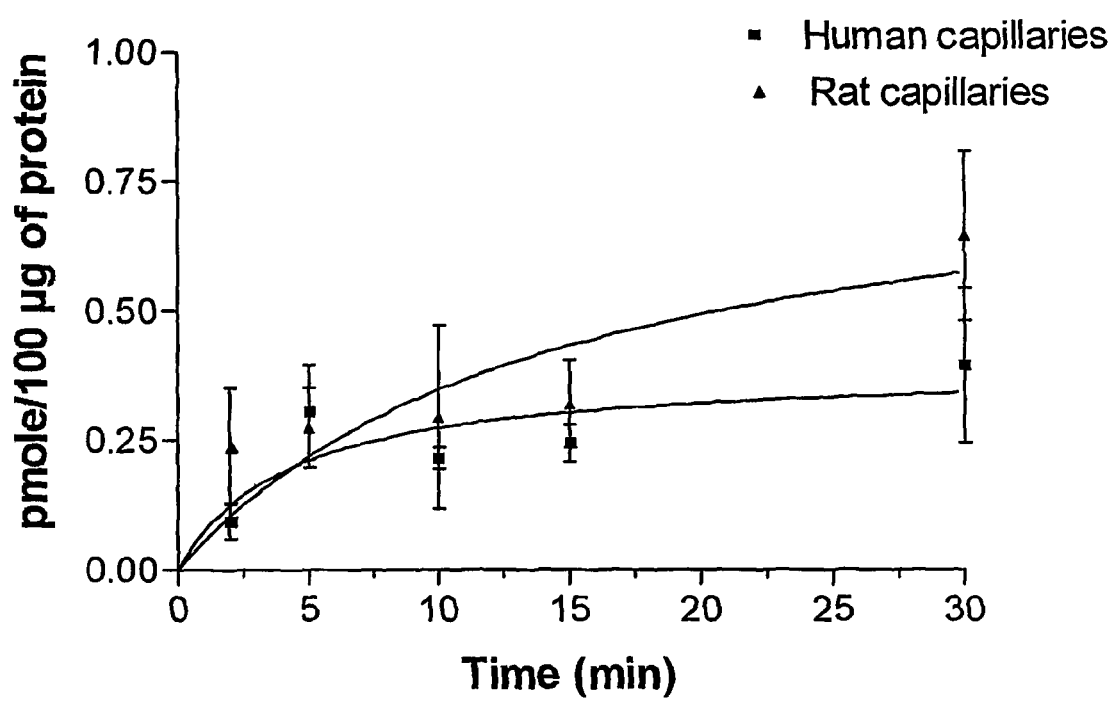
FIG. 9 is a plot illustrating a time-course of aprotinin uptake in human and rat capillaries

Aprotinin uptake was measured at 37° C. for variable time. Incubation medium contained aprotinin at a final 100 nM concentration in Ringer/Hepes solution. At each time point, accumulation was stopped by addition of ice-cold stop-solution and filtration in vacuum through a 0.45 μM filter. At each time point, nonspecific binding of aprotinin to the capillaries surface was evaluated by the addition of the ice-cold solution before adding the incubation medium. The results of this experiment are shown in FIG. 9.

Aprotinin-Biotin Conjugate: Biotinylation Procedure

Water soluble biotin analog Sulfo-NHS-LC-LC-Biotin (Pierce) was used for conjugation. This analog reacts with primary amines in the absence of organic solvent and at neutral pH. A 12-fold molar excess of biotin analog was added to a 10 mg/ml aprotinin solution. Biotin analog and aprotinin mix was incubated for 2 hours at 4° C. To remove unreacted biotin reagent, a dialysis was performed overnight in a slide-a-lyzer dialysis cassette (Pierce) with a 3500 Da cut-off. Determination of biotin incorporation was then performed with the dye HABA (2-(4'-hydroxyazobenzene)-benzoic acid) that binds to avidin yielding an absorption at 500 nm. This binding can be displaced with free biotin or with a biotinylated protein, allowing quantitation of biotin incorporation. The ratio obtained for this conjugation was three biotin for each aprotinin.

Aprotinin-Biotin Conjugate and Aprotinin have the same Transcytosis Capacity

Figure 10:
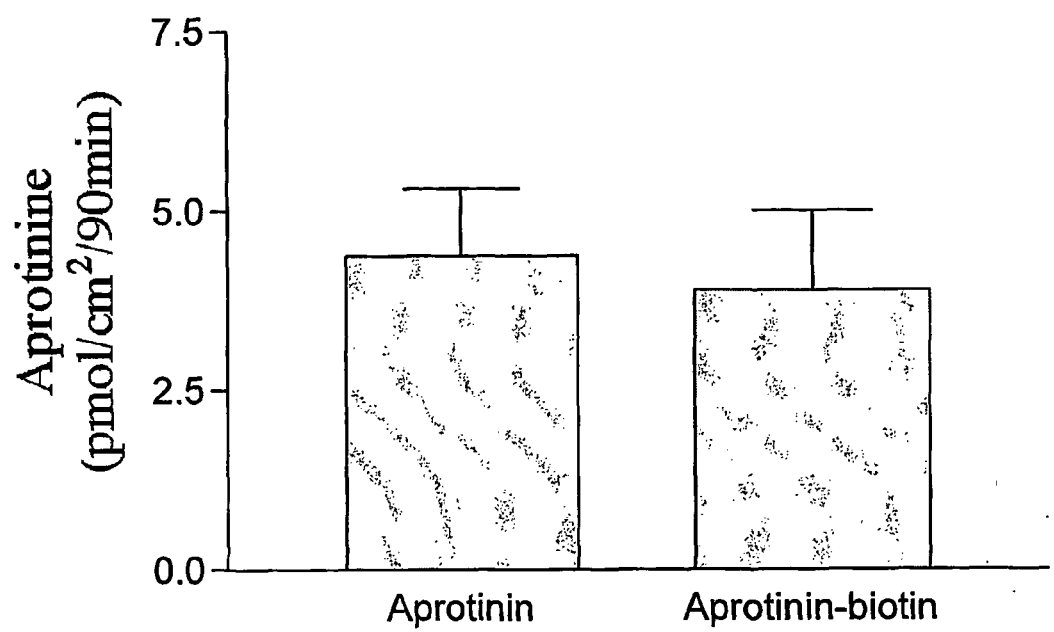
FIG. 10 is a bar graph illustrating that aprotinin-biotin conjugate and aprotinin have the same transcytosis capacity.

Transcytosis of [$^{125}$I]-aprotinin and [$^{125}$I]-aprotinin-biotin was evaluated at 37° C. [$^{125}$I]-protein (0.5-1.5 μCi/assay) at a final concentration of 250 nM was added to the upper side of the cell-covered filter for transcytosis measurement. At the end of the experiment, [$^{125}$I]-protein cellular transcytosis was determined directly by TCA precipitation. The results of this experiment are shown in FIG. 10.

Figure 11:
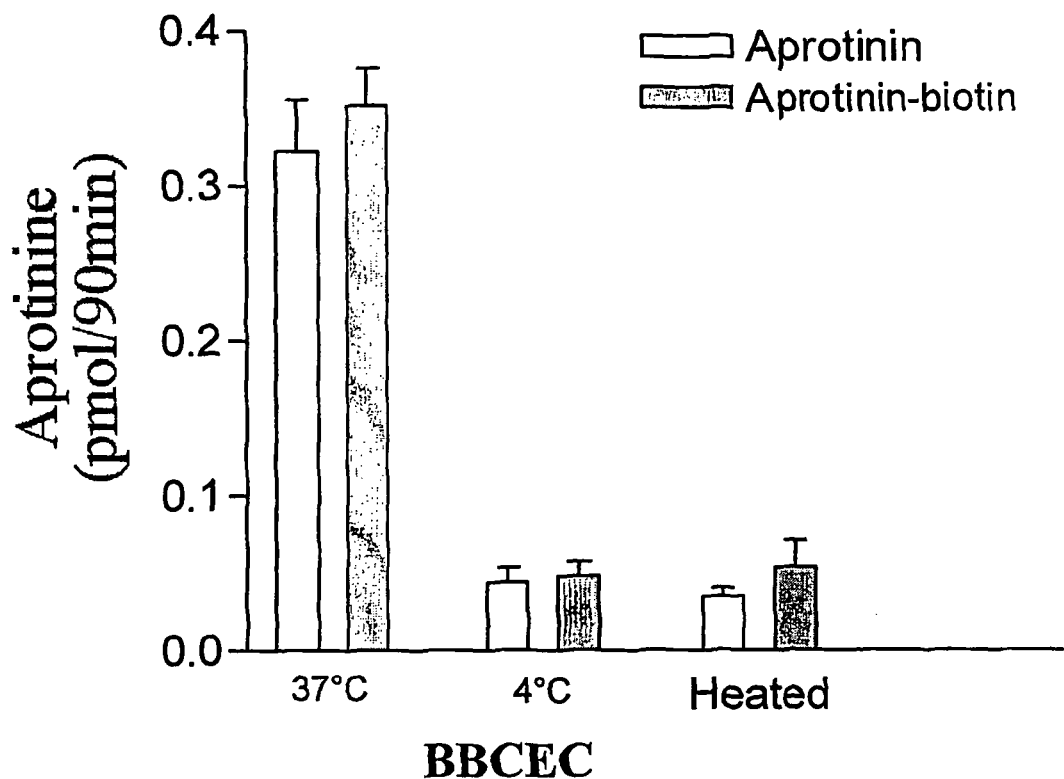
FIG. 11 is a bar graph illustrating that aprotinin and aprotinin-biotin conjugate transcytosis is temperature-dependent and conformational-dependent.

Aprotinin and Aprotinin-Biotin Conjugate Transcytosis is Temperature-Dependent and Conformational-Dependent Accumulation of [$^{125}$I]-aprotinin and [$^{125}$I]-aprotinin-biotin was evaluated at 37° C. and 4° C., or at 37° C. after proteins had been boiled for 10 min at 100° C. [$^{125}$I]-protein (0.5-1.5 µCi/assay) at a final concentration of 250 nM was added to the upper side of the cell-covered filter for transcytosis measurement. At the end of the experiment, cell-covered filters were cut and [$^{125}$I]-protein cellular accumulation was determined directly by TCA precipitation. The results of this experiment are shown in FIG. 11.

Figure 12A:
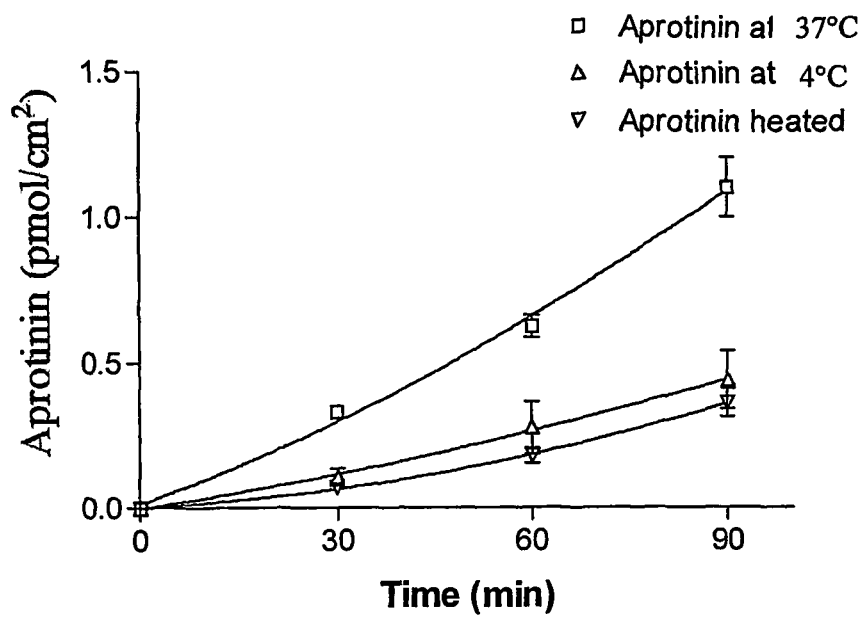
FIGS. 12A and 12B are sets of plots illustrating the effect of temperature and heating on (A) aprotinin and (B) aprotinin-biotin conjugate transcytosis in BBCEC cells.
Figure 12B:
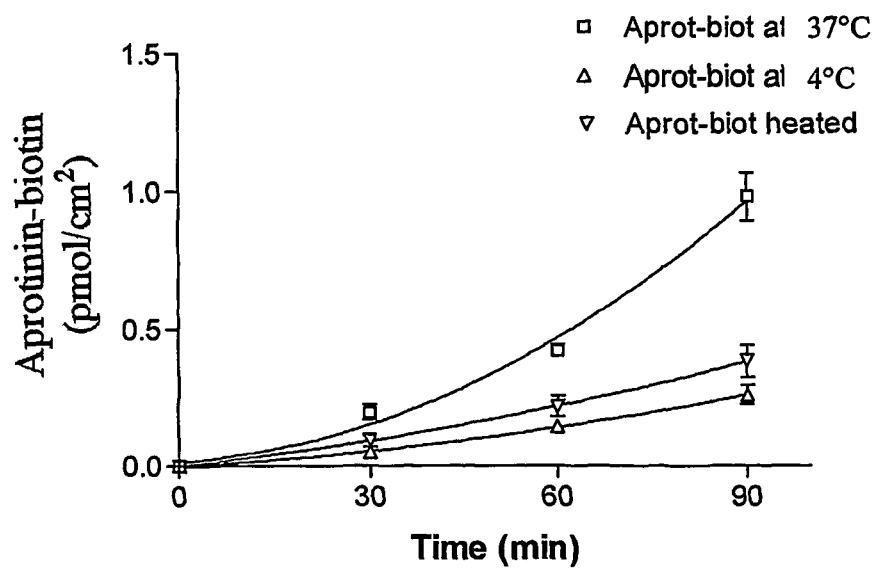

Effect of Temperature and Heating on Aprotinin and Aprotinin-Biotin Conjugate Transcytosis in BBCEC Cells Transcytosis of [$^{125}$I]-aprotinin (FIG. 12A) and [$^{125}$I]-aprotinin-biotin (FIG. 12B) was evaluated at 37° C. and 4° C., or at 37° C. after proteins had been boiled for 10 min at 100° C. [$^{125}$I]-protein (0.5-1.5 µCi/assay) at a final concentration of 250 nM was added to the upper side of the cell-covered filter for transcytosis measurement. At each time point filter was moved to the next well of the 6-well plate. At the end of the experiment, [$^{125}$I]-protein was assessed in the lower compartment of each well by TCA precipitation.

Figure 13:
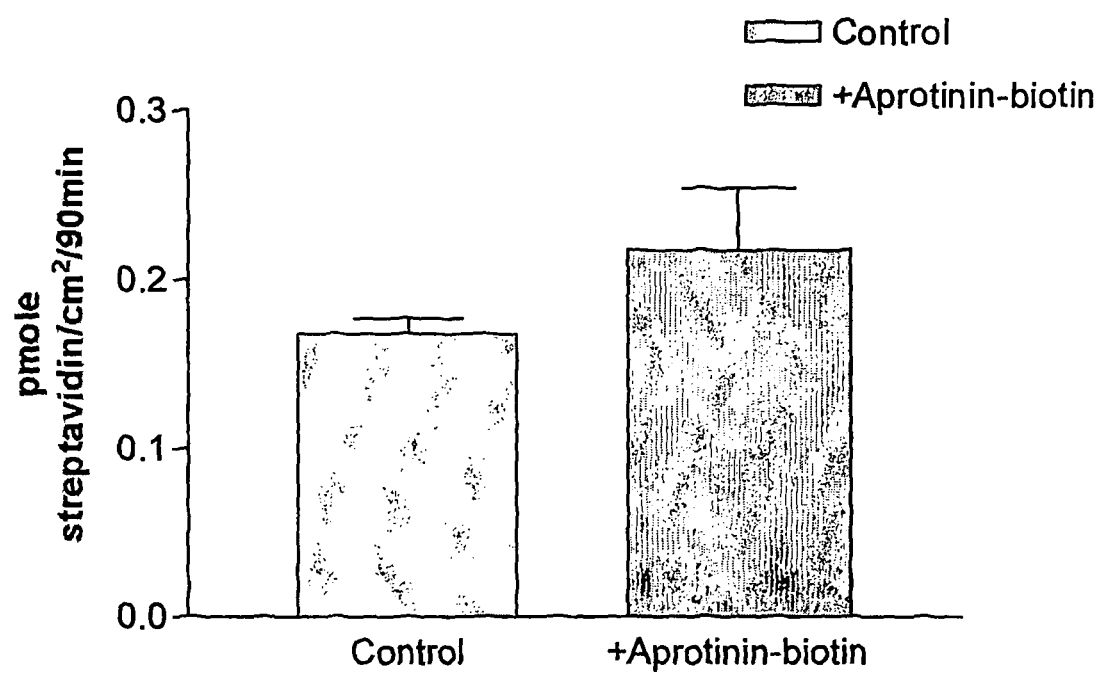
FIG. 13 is a bar graph illustrating the increase in streptavidin transcytosis in the presence of aprotinin-biotin conjugate.

Increase in Streptavidin Transcytosis in the Presence of Aprotinin-Biotin Conjugate Transcytosis of [$^{125}$I]-streptavidin was evaluated alone or in the presence of aprotinin-biotin conjugate. [$^{125}$I]-protein (0.5-1.5 µCi/assay) at a final concentration of 250 nM was added to the upper side of the cell-covered filter for transcytosis measurement. At each time point filter was moved to the next well of the 6-well plate. At the end of the experiment, [$^{125}$I]-protein was assessed in the lower compartment of each well by TCA precipitation. The results of this experiment are shown in FIG. 13.

Inhibition of Aprotinin Transcytosis by the LRP Antagonist, Receptor-Associated Protein (RAP)

Figure 14:
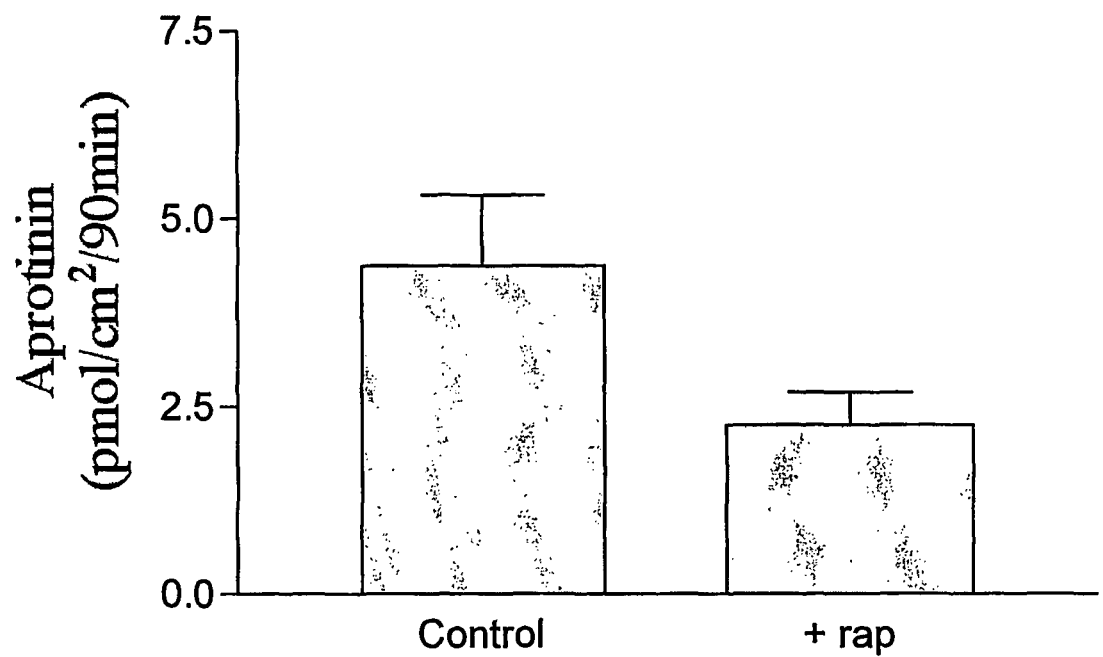
FIG. 14 is a bar graph illustrating the inhibition of aprotinin transcytosis by the LRP antagonist, receptor-associated protein (RAP)

Protein transcytosis was evaluated at 37° C. [$^{125}$I]-aprotinin (0.5-1.5 µCi/assay) at a final concentration of 250 nM was added to the upper side of the cell-covered filter with or without rap. At the end of the experiment, [$^{125}$I]-aprotinin was assessed in the lower compartment of each well by TCA precipitation. The results of this experiment are shown in FIG. 14.

Aprotinin Uptake: in situ Mouse Brain Perfusion

Surgical Procedure

The uptake of [$^{125}$I]-aprotinin to the luminal side of mouse brain capillaries was measured using the in situ brain perfusion method adapted in our laboratory for the study of drug uptake in the mouse brain (Dagenais et al., 2000, J. Cereb. Blood Flow Metab. 20(2):381-386). Briefly, the right common carotid of ketamine/xylazine (140/8 mg/kg i.p.) anesthetized mice was exposed and ligated at the level of the bifurcation of the common carotid, rostral to the occipital artery. The common carotid was then catheterized rostrally with polyethylene tubing (0.30 mm i.d.×0.70 mm o.d.) filled with heparin (25 U/ml) and mounted on a 26-gauge needle. The syringe containing the perfusion fluid (10 nM of [$^{125}$I]-aprotinin in Krebs/bicarbonate buffer at a pH7.4 gassed with 95% $O_2$ and 5% $CO_2$) was placed in an infusion pump (Harvard pump PHD 2000; Harvard Apparatus) and connected to the catheter. Immediately before the perfusion, the heart was stopped by severing the ventricles to eliminate contralateral blood flow contribution. The brain was perfused for 10 min at a flow rate of 2.5 ml/min. After 10 min of perfusion, the brain was further perfused for 30 s with Ringer/HEPES solution (150 mM NaCl, 5.2 mM KCl, 2.2 mM $CaCl_2$, 0.2 mM $MgCl_2$, 6 mM $NaHCO_3$, 5 mM HEPES, 2.8 mM glucose, pH 7.4), to wash the excess of [$^{125}$I]-aprotinin. Mice were then decapitated to terminate perfusion and the right hemisphere was isolated on ice before being subjected to capillary depletion (Triguero et al., 1990, J Neurochem. 54(6):1882-8). Aliquots of homogenates, supernatants, pellets and perfusates were taken to measure their contents in [$^{125}$I]-aprotinin by TCA precipitation and to evaluate the apparent volume of distribution.

Determination of BBB Transport Constants

Briefly, calculations were carried out as previously described by Smith (1996, Pharm. Biotechnol. 8:285-307). Aprotinin uptake was expressed as the volume of distribution ($V_d$) from the following equation:

$$Vd=Q^*_{br}/C^*_{pf}$$

where $Q^*_{br}$ is the calculated quantity of [$^{125}$I]-aprotinin per gram of right brain hemisphere and $C^*_{pf}$ is the labeled tracer concentration measured in the perfusate.

Figure 15:
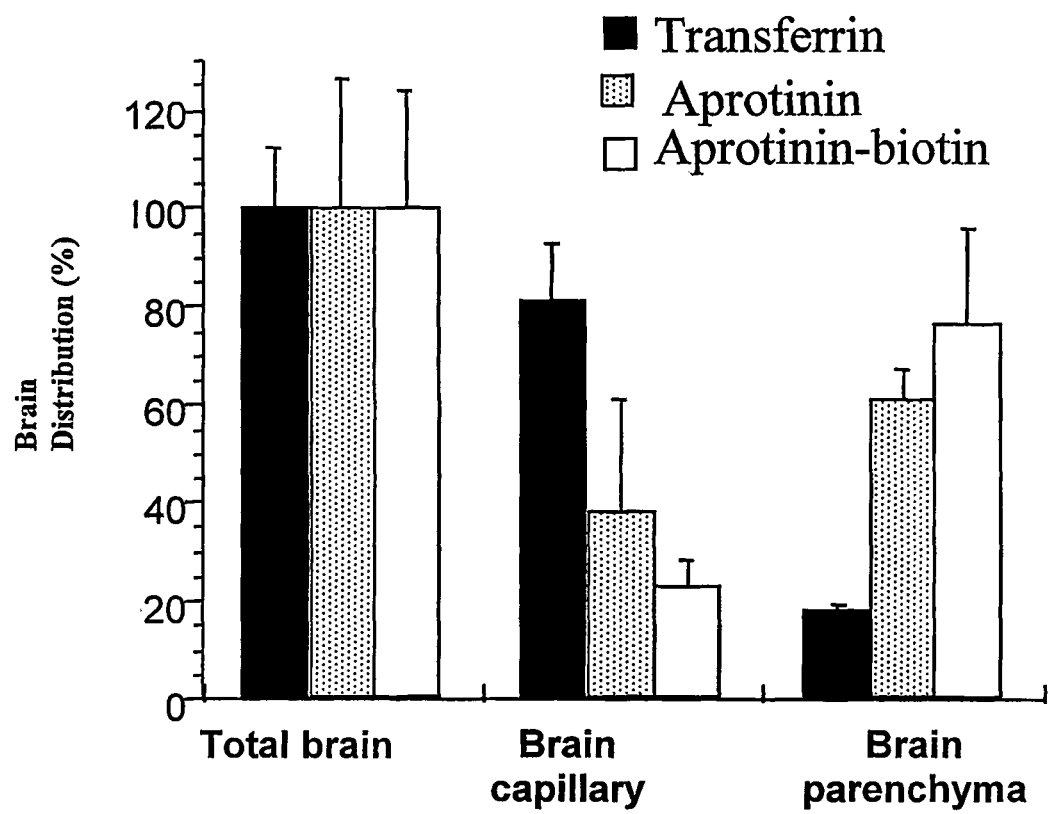
FIG. 15 is a bar graph illustrating aprotinin uptake in an in situ brain perfusion experiment.

The results of this experiment, shown in FIG. 15, indicate that there is higher brain uptake for aprotinin than transferrin and that conjugation with biotin does not modify brain uptake of aprotinin.

In view of the results obtained for the above-mentioned tests, aprotinin is a promising carrier for transporting an agent or compound across the BBB since it has a higher transcytosis across BBCEC monolayers than that of other proteins and it does not alter the integrity of the blood-brain barrier. In addition, aprotinin is not degraded during transcytosis nor does conjugation of aprotinin to biotin affect its transcytosis. Moreover, aprotinin is a versatile and flexible carrier since many molecules such as small drug molecules, proteins, peptides and enzymes may be easily attached to aprotinin proteins for promoting their passage across the BBB. These molecules can conceivably be attached to aprotinin via a linker.

It has also been determined that the brain distribution volume of aprotinin is higher than that of transferrin. It has further been determined that transcytosis is temperature sensible and conformation dependent, implying that a LDL-R family receptor, probably LRP is involved in aprotinin transcytosis.

Thus, aprotinin is an effective and efficient carrier to deliver an agent into the brain through the blood-brain barrier.

Design of a Peptide as a Drug Vector for the Brain

Figure 16:
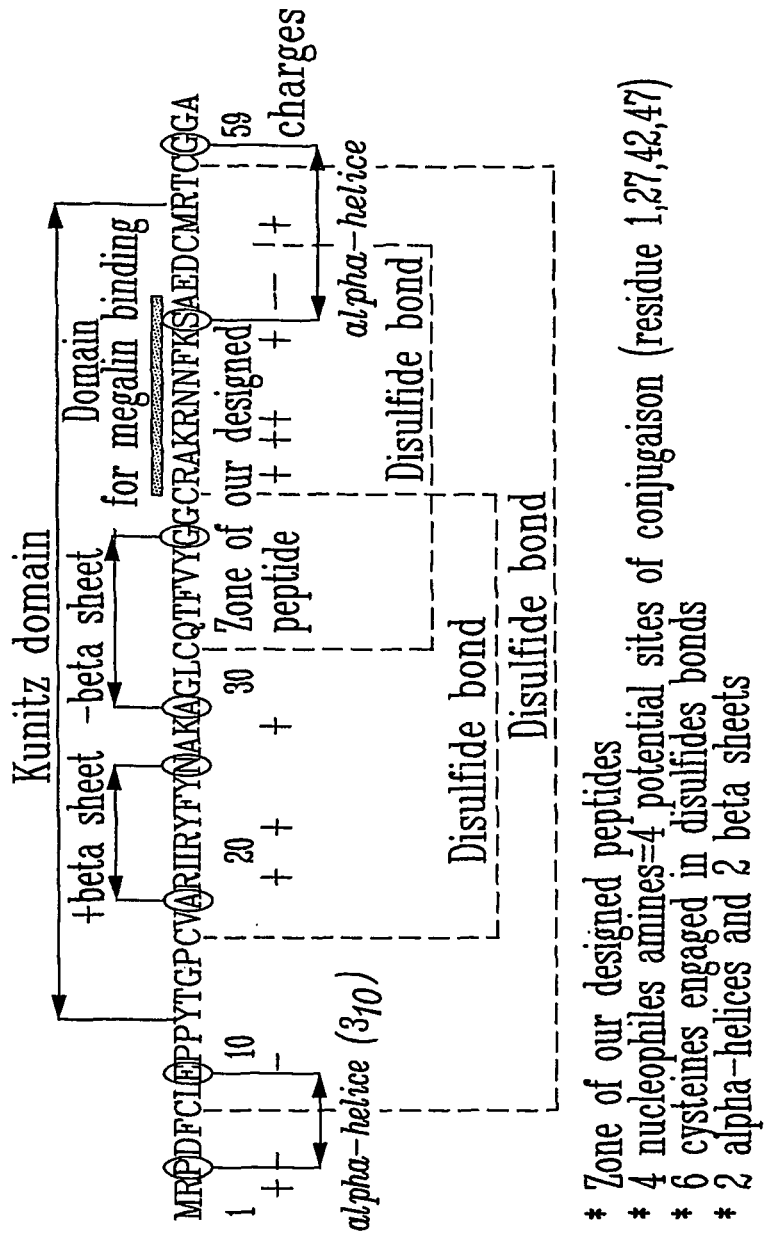
FIG. 16 illustrates a synthetic-aprotinin sequence (SEQ ID NO:5)

A sequence comparison was made on the N-terminal sequence of aprotinin (MRPDFCLEPPYTGPCVARIIR) (FIG. 16) (SEQ ID NO:2) using the BLAST™ program on the National Center for Biotechnology Information (NCBI) website. This sequence comparison resulted in four sequences being identified. None of these identified sequences corresponded to a human protein.

Figure 17:
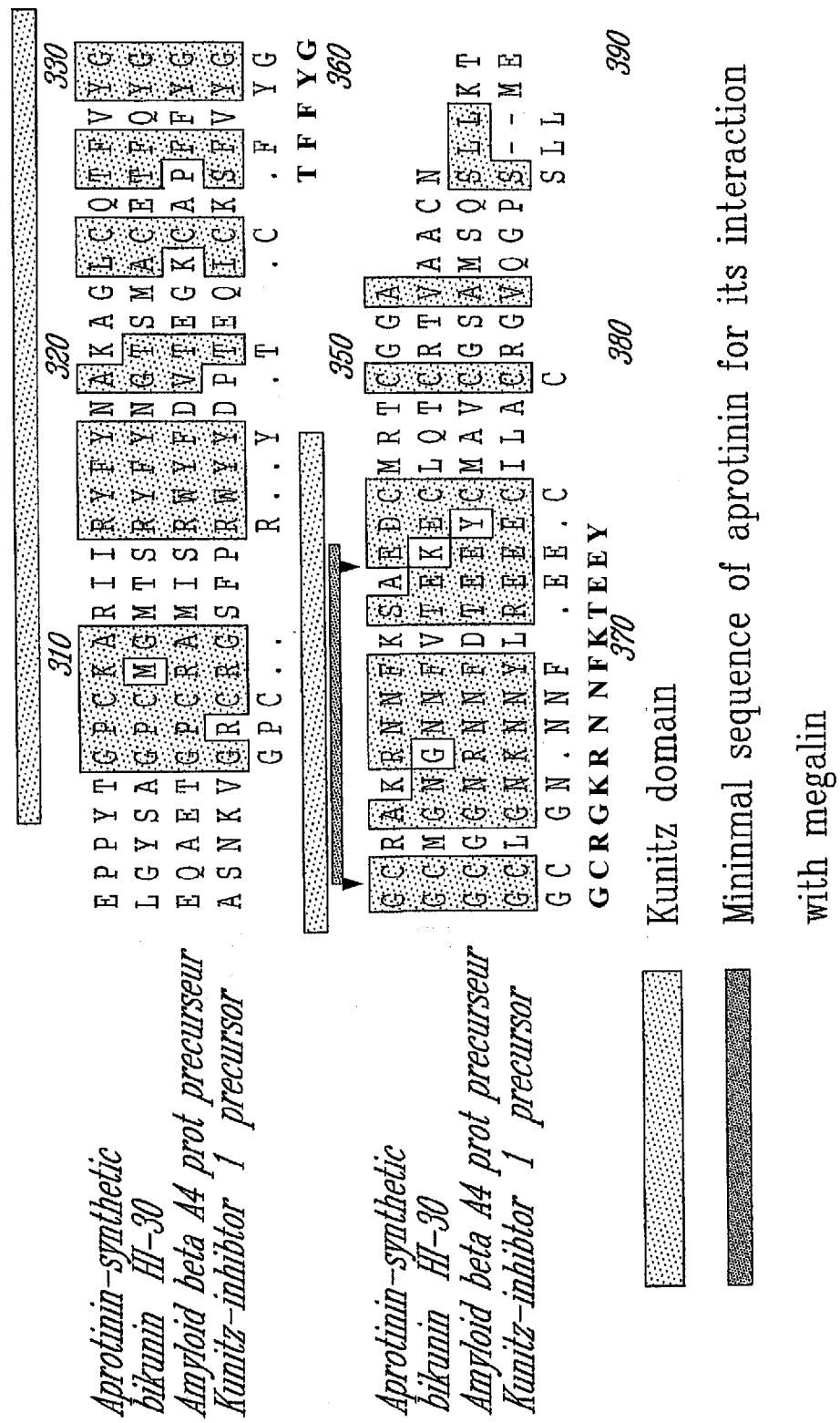
FIG. 17 illustrates a sequence alignment between aprotinin (SEQ ID NO:6)and three human proteins with a similar domain (SEQ ID NOS:7-9)

The C-terminal sequence of aprotinin (GLCQTFVYG-GCRAKRNNFKSAE) (FIG. 16) (SEQ ID NO:3) was also compared on the NCBI website. This sequence comparison resulted in 27 sequences being identified with some corresponding to human proteins. The proteins with the highest score were then aligned with the sequence of aprotinin (FIG. 17). From this alignment, the following Angio-pep1 peptide was generated: TFFYGGCRGKRNNFKTEEY (net charge+ 2) (SEQ ID NO:4).

In situ Brain Perfusion of Transferrin, Aprotinin and Angio-pep1

Figure 18:
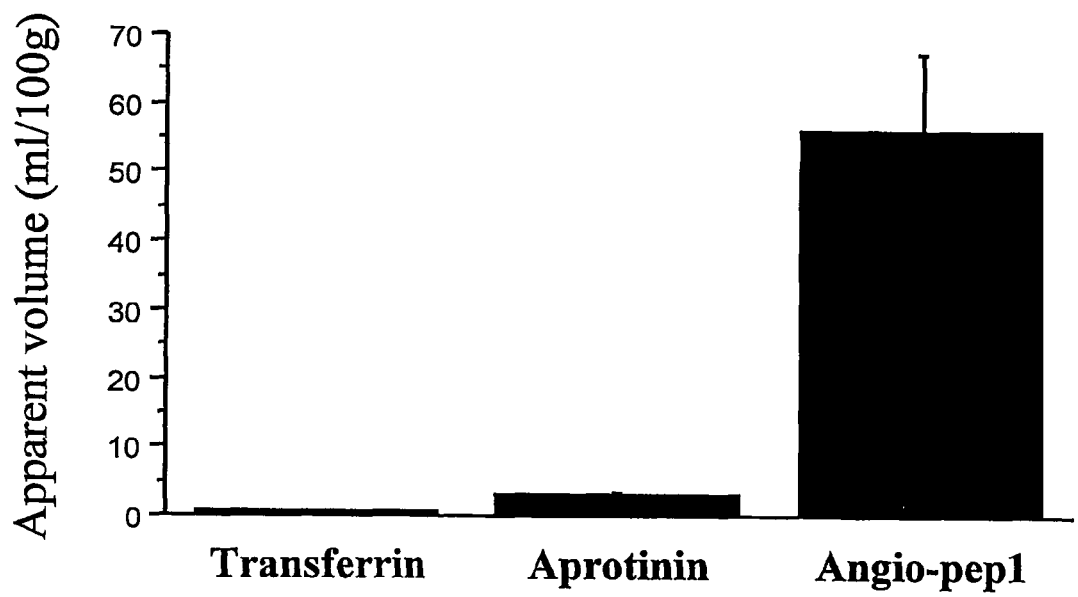
FIG. 18 is a bar graph illustrating in situ brain perfusion of transferrin, aprotinin and Angio-pep1.

The brain apparent volume of distribution was measured for [$^{125}$I]-transferrin, [$^{125}$I]-aprotinin and [$^{125}$I]-Angio-pep1. Mice brains were perfused for 10 min. Brain capillary depletion was performed to assess the apparent volume of distribution in the brain parenchyma. The results of this experiment are shown in FIG. 18.

Transcytosis of Angio-pep1 Compared to that of Aprotinin

Figure 19:
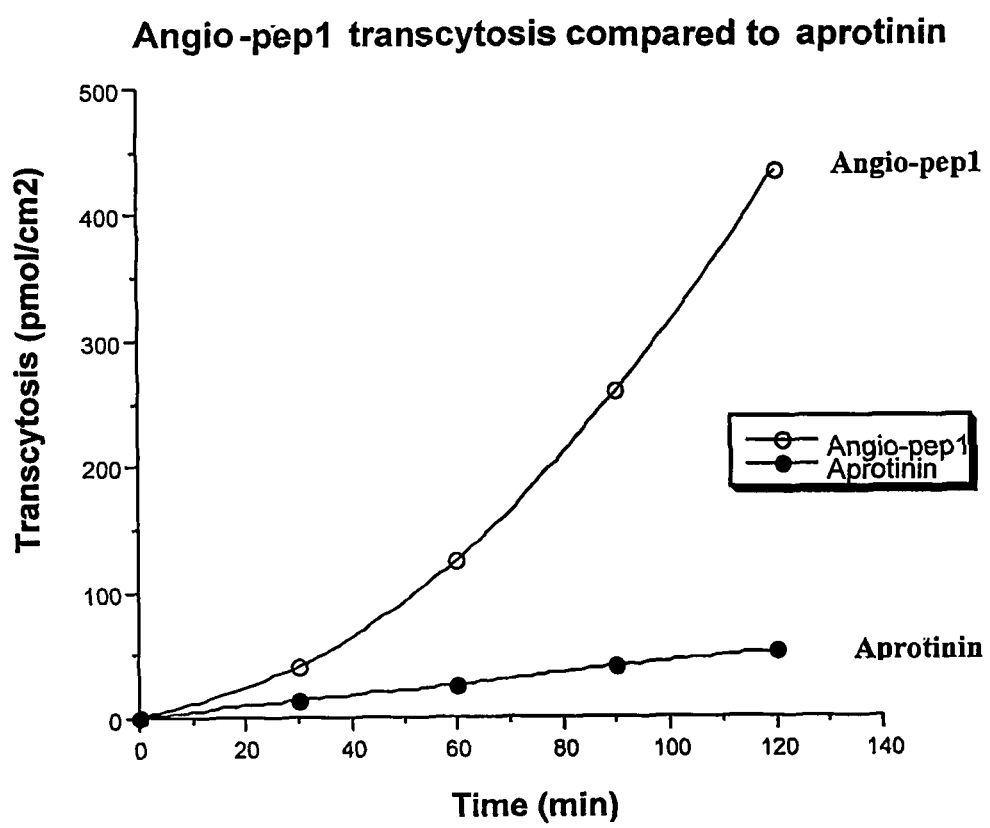
FIG. 19 is a plot illustrating transcytosis of Angio-pep1 compared to that of aprotinin.

Transcytosis of Angio-pep1 was compared to that of aprotinin. Transport of [$^{125}$I]-Angio-pep1 and [$^{125}$I]-aprotinin from the apical-to-basolateral side of endothelial cells monolayers was measured as described above. The final concentration used for angiopep1 and aprotinin for this experiment was 2.5 µM. The results of this experiment are shown in FIG. 19.

Transcytosis of Angio-pep1 across the in vitro Blood-Brain Barrier Model

Figure 20:
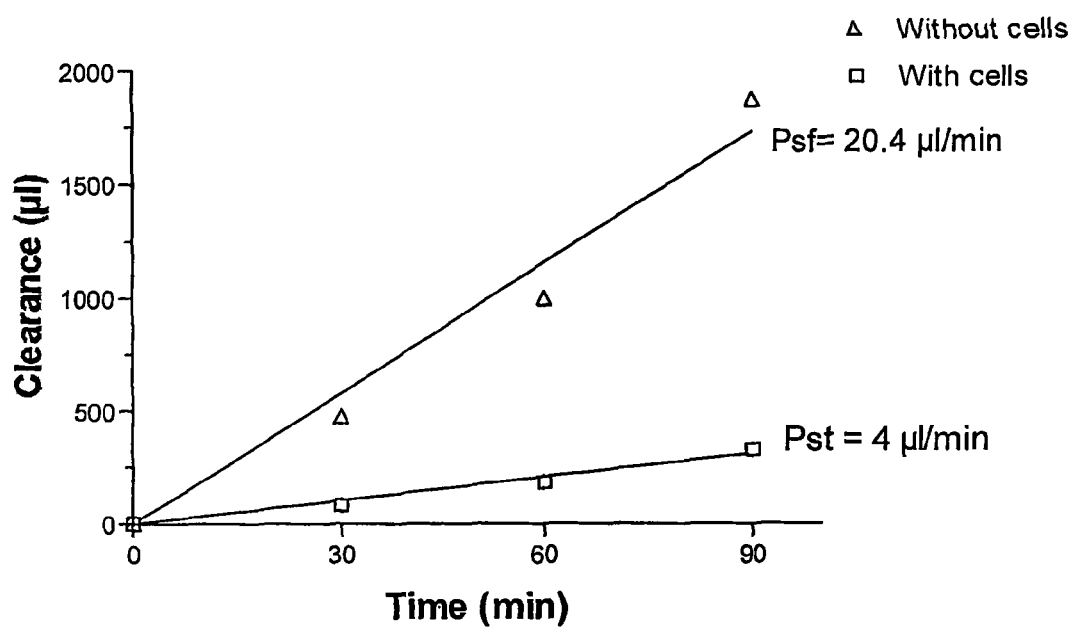
FIG. 20 is a plot illustrating transcytosis of Angio-pep1 across the in vitro blood-brain barrier model.

The transport of Angio-pep1 from the apical-to-basolateral side of inserts covered with or without endothelial cell monolayers was measured. The results are expressed as the clearance of Angio-pep1 as a function of time. The slopes correspond to the permeability of the peptide through the filter alone (Psf) and to the total permeability of the endothelial cell monolayers (Pst). The permeability coefficient (Pe) for Angio-pep1 was $1.2 \times 10^{-3}$ cm/min. The results of this experiment are shown in FIG. 20.

The permeability coefficients for Angio-pep1, aprotinin, leptin and transferrin were determined using the in vitro blood-brain barrier model. The permeability coefficient (Pe) was calculated as described above. The comparison of the permeability coefficients is shown in Table 4.

TABLE 4

Permeability coefficients for Angio-pep1, aprotinin, leptin and transferrin

| Proteins | Permeability coefficient (Pe) ($\times 10^{-3}$ cm/min) | Ratios |
| --- | --- | --- |
| Angio-pep1 | 1.2 | 1 |
| Aprotinin | 0.16 | 7.5 |
| Leptin | 0.055 | 21 |
| Transferrin | 0.0057 | 210 |

The above experiments indicate that brain penetration for Angio-pep1 is higher than that of aprotinin and transferrin. The experiments also indicate that transcytosis of Angio-pep1 measured using the in vitro blood-brain barrier model is higher than that of other proteins including aprotinin, leptin and transferrin.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An isolated carrier, wherein the brain penetration or transcytosis across the blood-brain barrier of said carrier is greater than that of aprotinin:
   (a) comprising AngioPep-1 (SEQ ID NO:4) or
   (b) consisting of a polypeptide having the amino acid sequence RGKRNNFKTEEY(residues 8-19 of SEQ ID NO:4).

2. The carrier of claim 1, consisting of a polypeptide having the amino acid sequence RGKRNNFKTEEY (residues 8-19 of SEQ ID NO:4).

3. The carrier of claim 1, comprising AngioPep-1.

4. The carrier of claim 3, consisting of AngioPep-1.

5. A conjugate comprising:
   (a) a carrier comprising AngioPep-1 (SEQ ID NO:4) or consisting of a polypeptide having the amino acid sequence RGKRNNFKTEEY (residues 8-19 or SEQ ID NO:4), wherein the brain penetration or transcytosis across the blood-brain barrier of said carrier is greater than that of aprotinin, and
   (b) an agent attached to said carrier, wherein said conjugate is able to cross the blood brain barrier.

6. The conjugate of claim 5, wherein the carrier consists of a polypeptide having the amino acid sequence RGKRNNFKTEEY (residues 8-19 of SEQ ID NO:4).

7. The conjugate of claim 5, wherein the carrier comprises AngioPep-1.

8. The conjugate of claim 5, wherein the carrier consists of AngioPep-1.

9. The conjugate of any of claims 5-8, wherein said agent has a maximum molecular weight of 160,000 Daltons.

10. The conjugate of claim 5, wherein said agent is selected from the group consisting of a drug, a medicine, a protein, a peptide, an enzyme, an antibiotic, an anti-cancer agent, a a radioimaging agent, an antibody, a cellular toxin, a detectable label, and an anti-angiogenic compound.

11. The conjugate of claim 10, wherein said drug is a small molecule drug having a molecular weight less than 1000 g/mol.

12. The conjugate of claim 10, wherein said agent is an anticancer agent.

13. The conjugate of claim 12, wherein said anticancer agent is paclitaxel.

14. The conjugate of claim 10, wherein said agent is an antibody.

15. The conjugate of claim 5, wherein transport of said conjugate across the blood-brain barrier does not affect blood-brain barrier integrity.

16. A pharmaceutical composition comprising a conjugate of claim 5 and a pharmaceutically acceptable excipient.

17. The pharmaceutical composition of claim 16, wherein said composition can be administered intra-arterially, intra-nasally, intra-peritoneally, intravenously, intramuscularly, sub-cutaneously, transdermally, or per os.

18. A method of transporting an agent across the blood-brain barrier, comprising the administration of the conjugate of claim 5.

19. A method of transporting an agent across a blood-brain barrier, which comprises the step of administering to an individual the pharmaceutical composition of claim 16.

20. The conjugate of claim 5, wherein said agent is a therapeutic agent.

* * * * *